(12) United States Patent
Roscoe et al.

(10) Patent No.: US 12,023,393 B2
(45) Date of Patent: Jul. 2, 2024

(54) POLYMERIZABLE 4,4'-SPIROBI[CHROMANE]-2,2'-DIONES AND CURABLE COMPOSITIONS INCLUDING THE SAME

(71) Applicant: Solventum Intellectual Properties Company, Maplewood, MN (US)

(72) Inventors: Stephen B. Roscoe, Woodbury, MN (US); Paul J. Homnick, Lake Elmo, MN (US); Ahmed S. Abuelyaman, Woodbury, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 0 days.

(21) Appl. No.: 18/281,229

(22) PCT Filed: Feb. 3, 2022

(86) PCT No.: PCT/IB2022/050958
§ 371 (c)(1),
(2) Date: Sep. 8, 2023

(87) PCT Pub. No.: WO2022/195364
PCT Pub. Date: Sep. 22, 2022

(65) Prior Publication Data
US 2024/0122815 A1 Apr. 18, 2024

Related U.S. Application Data

(60) Provisional application No. 63/162,279, filed on Mar. 17, 2021.

(51) Int. Cl.
*A61K 6/891* (2020.01)
*C07D 493/10* (2006.01)

(52) U.S. Cl.
CPC ............ *A61K 6/891* (2020.01); *C07D 493/10* (2013.01)

(58) Field of Classification Search
CPC ...................................................... A61K 6/891
See application file for complete search history.

(56) References Cited

U.S. PATENT DOCUMENTS

| | | | |
|---|---|---|---|
| 1,750,299 | A | 3/1930 | Dohme |
| 4,071,424 | A | 1/1978 | Dart et al. |
| 4,356,296 | A | 10/1982 | Griffith et al. |
| 4,503,169 | A | 3/1985 | Randklev |
| 4,642,126 | A | 2/1987 | Zador et al. |
| 4,652,274 | A | 3/1987 | Boettcher et al. |
| 4,661,601 | A | 4/1987 | Howell |
| 4,695,251 | A | 9/1987 | Randklev |
| 4,772,530 | A | 9/1988 | Gottschalk et al. |
| 4,874,450 | A | 10/1989 | Gottschalk |
| 4,954,414 | A | 9/1990 | Adair et al. |
| 5,055,372 | A | 10/1991 | Shanklin |
| 5,057,393 | A | 10/1991 | Shanklin et al. |
| 5,076,844 | A | 12/1991 | Fock et al. |
| 5,081,197 | A | 1/1992 | Heilmann et al. |
| 5,545,676 | A | 8/1996 | Palazzotto et al. |
| 6,387,981 | B1 | 5/2002 | Zhang et al. |
| 6,572,693 | B1 | 6/2003 | Wu et al. |
| 7,156,911 | B2 | 1/2007 | Kangas |
| 7,649,029 | B2 | 1/2010 | Kolb et al. |
| 8,647,510 | B2 | 2/2014 | Kolb et al. |

(Continued)

FOREIGN PATENT DOCUMENTS

| | | |
|---|---|---|
| EP | 0173567 A2 | 3/1986 |
| EP | 0201778 B1 | 12/1988 |

(Continued)

OTHER PUBLICATIONS

Dixit, "Condensation of Phenols and Phenolic Ethers with Acetone Dicarboxylc Acid. Use of Condensing Agents Other Than Sulphuric Acid. A New Non-Acidic Condensation Product", Jul. 1945, Journal of the Indian Chemical Society. vol 22, No. 7, pp. 207-213.

Dixit, "Sulphuryl chloride: A New Condensing Agent for the Pechmann-Reaction. Isolation of Trans β-2: 4-Dihydroxy-Phenyl-Glutaconic Acid", 1948, Proceedings of the Indian Academy of Sciences—Section A 27, Art. 14, pp. 14-22.

Dubovik, "4,4'-Spirodichroman-2-Ones as Unexpected Products from the Condensation of Resorcinols and Dimethyl Acetonedicarboxylate", 2007, Chemistry of Heterocyclic Compounds, vol. 43, No. 3, pp. 277-281.

(Continued)

*Primary Examiner* — Benjamin J Packard

(57) ABSTRACT

A polymerizable compound is represented by the formula (I). Each $R^1$ independently represents a monovalent group having from 3 to 12 carbon atoms that comprises at least one of an epoxy group, an acryl group, or a methacryl group. Each $R^2$ independently represents H, F, Cl, Br, $C_1$-$C_{12}$ alkyl, $C_2$-$C_3$ carbonylalkyl, or $C_2$-$C_5$ carboalkoxy. Each $R^3$ independently represents H, F, Cl, Br, $C_1$-$C_{12}$ alkyl, $C_2$-$C_3$ carbonylalkyl, or $C_2$-$C_5$ carboalkoxy. Each n is independently 0, 1, 2, 3, or 4. Curable compositions including the polymerizable compound are also disclosed.

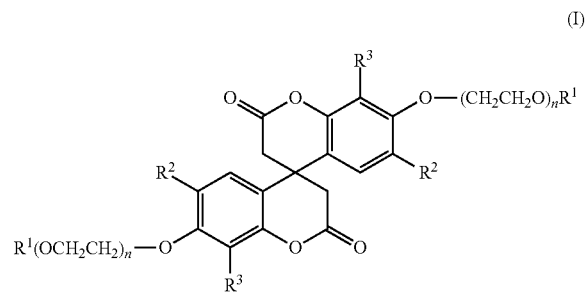

(I)

20 Claims, No Drawings

(56) References Cited

U.S. PATENT DOCUMENTS

| | | |
|---|---|---|
| 9,320,685 B2 | 4/2016 | Moser et al. |
| 9,907,733 B2 | 3/2018 | Joly et al. |
| 2007/0197750 A1 | 8/2007 | Gibanel et al. |
| 2020/0383877 A1 | 12/2020 | Kobussen et al. |

FOREIGN PATENT DOCUMENTS

| | | |
|---|---|---|
| EP | 0201031 B1 | 8/1989 |
| EP | 0373384 B1 | 10/1992 |
| WO | 2000038619 A2 | 7/2000 |
| WO | 2000042092 A1 | 7/2000 |
| WO | 2001007444 A1 | 2/2001 |
| WO | 2001030305 A1 | 5/2001 |
| WO | 2001030306 A1 | 5/2001 |
| WO | 2001030307 A1 | 5/2001 |
| WO | 2001092271 A1 | 12/2001 |
| WO | 2003063804 A1 | 8/2003 |
| WO | 2005123872 A1 | 12/2005 |
| WO | 2008101806 A2 | 8/2008 |
| WO | 2016014536 A1 | 1/2016 |
| WO | 2022112886 A1 | 6/2022 |

OTHER PUBLICATIONS

International Search Report received for PCT International Application No. PCT/IB2022/050958, dated Apr. 5, 2022, 5 pages.

Paunescu, "A Versatile Access to New Halogenated 7-azidocoumarins for Photoaffinity Labeling: Synthesis and Photophysical Properties", 2011, Dyes and Pigments, vol. 91, pp. 427-434.

Ronald, "Craig's Restorative Dental Materials—Testing of Dental Materials and Biomechanics ", 2012, Elsevier, p. 86.

Wodtke, "Evaluation of Novel Fluorescence Probes for Conjugation Purposes Using the Traceless Staudinger Ligation", 2015, Dyes and Pigments, vol. 113, pp. 263-273.

POLYMERIZABLE 4,4'-SPIROBI[CHROMANE]-2,2'-DIONES AND CURABLE COMPOSITIONS INCLUDING THE SAME

CROSS REFERENCE TO RELATED APPLICATIONS

This application is a national stage filing under 35 U.S.C. § 371 of PCT/IB2022/050958, filed Feb. 3, 2022, which claims the benefit of Provisional Application No. 63/162,279, filed Mar. 17, 2021, the disclosure of which is incorporated by reference in its/their entirety herein.

BACKGROUND

Polymerizable compounds such as epoxides and (meth)acrylated compounds are widely used in fields such as protective and/or decorating coatings, adhesives, molding, rapid prototyping, and dental restoratives. There is a continuing need for new polymerizable compounds that can impart beneficial properties to compositions containing them before and/or after polymerization.

SUMMARY

The present disclosure provides polymerizable compounds having a spiro-fused aromatic central core (i.e., a 2,2'-diketo-4,4'-bi[chromane] moiety). The polymerizable compounds are relatively easy and inexpensive to make and may exhibit after polymerization at least one of reduced shrinkage and/or improved adhesive properties.

In a first aspect, the present disclosure provides a polymerizable compound represented by the formula

[Structural formula showing spirobi[chromane]-dione with substituents $R^1(OCH_2CH_2)_n$—O, $R^2$, $R^3$, and O—$(CH_2CH_2O)_nR^1$]

wherein
each $R^1$ independently represents a monovalent group having from 3 to 12 carbon atoms that comprises at least one of an epoxy group, an acryl group, or a methacryl group;
each $R^2$ independently represents H, F, Cl, Br, $C_1$-$C_{12}$ alkyl, $C_2$-$C_3$ carbonylalkyl, or $C_2$-$C_5$ carboalkoxy;
each $R^3$ independently represents H, F, Cl, Br, $C_1$-$C_{12}$ alkyl, $C_2$-$C_3$ carbonylalkyl, or $C_2$-$C_5$ carboalkoxy; and
each n is independently 0, 1, 2, 3, or 4.

The polymerizable compound is useful, for example, in curable compositions.

Accordingly, in a second aspect, the present disclosure provides a curable composition comprising:
a polymerizable compound according to the present disclosure; and
a curative (for example, a free radical initiator or an epoxy curative) for the polymerizable compound.

As used herein:
the expression "Cm-Cn" wherein means having from m to n carbon atoms, inclusive; and
the prefix "(meth)acryl" refers to acryl and/or methacryl.

Features and advantages of the present disclosure will be further understood upon consideration of the detailed description as well as the appended claims.

DETAILED DESCRIPTION

Polymerizable compounds according to the present disclosure can be represented by the structural formula:

[Structural formula showing spirobi[chromane]-dione with substituents $R^1(OCH_2CH_2)_n$—O, $R^2$, $R^3$, and O—$(CH_2CH_2O)_nR^1$]

Each $R^1$ independently represents a monovalent group having from 3 or 4 to 12 carbon atoms, in some embodiments 3 or 4 to 10 carbon atoms, and in some embodiments 3 or 4 to 6 carbon atoms. Each $R^1$ may comprise at least one of an epoxy group, an acryl group, or a methacryl group (e.g., as part of a (meth)acryloxy, (meth)acrylamido, N-methylacrylamido, N-ethylacrylamido, (meth)acrylthio, or (meth)acrylalkyl group). Preferably, both $R^1$ groups are the same as it simplifies preparation, but they may also be different.

Each n is independently 0, 1, 2, 3, or 4. In the case where n=0, the $R^1$ group is bonded directly to the O atom bonded to the aromatic ring. Preferably, both n are the same, but they may also be different.

Exemplary groups $R^1$ include:

$$-\overset{O}{\underset{\|}{C}}-\overset{H}{\underset{}{N}}-(CH_2CH_2O)_x-\overset{O}{\underset{\|}{C}}-\overset{R^4}{\underset{}{C}}=CH_2$$

wherein R is H or methyl, x is 1 or 2;

$$-\overset{O}{\underset{\|}{C}}-\overset{CH_3}{\underset{CH_3}{\overset{|}{C}}}-\overset{H}{\underset{}{N}}-\overset{O}{\underset{\|}{C}}-\overset{R^4}{\underset{}{C}}=CH_2$$

wherein $R^4$ is H or methyl;

$$-CH_2\overset{OH}{\underset{}{C}}HCH_2O\overset{O}{\underset{\|}{C}}-\overset{R^4}{\underset{}{C}}=CH_2$$

wherein $R^4$ is H or methyl; and $$-\overset{O}{\underset{\|}{C}}-\overset{R^4}{\underset{}{C}}=CH_2$$

wherein $R^4$ is H or methyl.

Each $R^2$ independently represents H, F, Cl, Br, $C_1$-$C_{12}$ alkyl (e.g., methyl, ethyl, propyl, isopropyl, butyl, isobutyl, pentyl, isopentyl, hexyl, cyclohexyl, octyl, decyl, or dodecyl), $C_2$-$C_3$ carbonylalkyl (e.g., acetyl or propanoyl), or $C_2$-$C_5$ carboalkoxy (e.g., carbomethoxy, carboethoxy, carbopropoxy, or carbobutoxy). Preferably, both $R^2$ groups are the same, but they may also be different.

Likewise, each $R^3$ independently represents H, F, Cl, Br, $C_1$-$C_{12}$ alkyl (e.g., methyl, ethyl, propyl, isopropyl, butyl, isobutyl, pentyl, isopentyl, hexyl, or cyclohexyl), $C_2$-$C_3$ carbonylalkyl (e.g., acetyl or propanoyl), or $C_2$-$C_5$ carboalkoxy (e.g., carbomethoxy, carboethoxy, carbopropoxy, or carbobutoxy). Preferably, both $R^3$ groups are the same, but they may also be different.

2,2'-Diketobi[chromane]s can be made by either of the convenient synthetic methods shown in Schemes I and II below:

SCHEME I

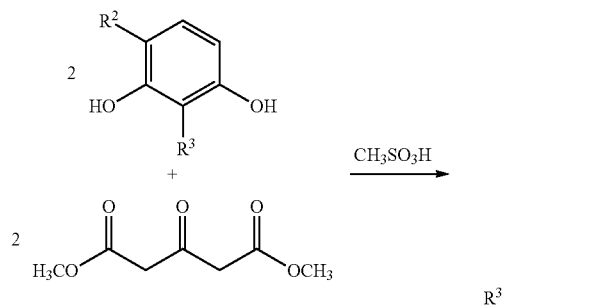

SCHEME 2

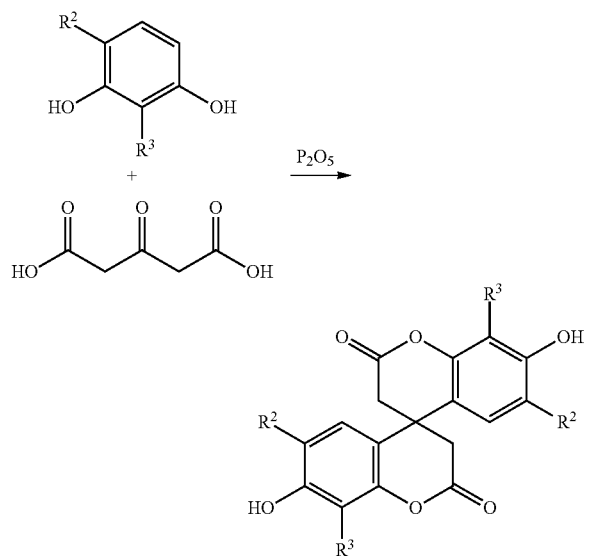

Condensation occurs in the presence of a suitable strong acid catalyst such as methanesulfonic acid or phosphorus pentoxide. Selection of appropriate corresponding resorcinols provides corresponding $R^2$ and $R^3$ groups. Where $R^2$ or $R^3$ is an electron-withdrawing group such as Cl, Br, or C(=O)OR, methanesulfonic acid may be an efficient catalyst. Where $R^2$ or $R^3$ is H or an electron-donating group such as ethyl, condensation using phosphorus pentoxide with acetonedicarboxylic acid may be preferred. Subsequent functionalization of the phenolic groups, generally using well-known techniques, provides the polymerizable compounds.

Exemplary commercially available resorcinols include resorcinol (i.e., 1,3-dihydroxybenzene), 2-fluororesorcinol, 4-fluororesorcinol, 2-chlororesorcinol, 4-chlororesorcinol, 2-bromoresorcinol, 4-bromoresorcinol, 2,4-difluororesorcinol, 2,4-dichlororesorcinol, 2,4-dibromoresorcinol, 2-methylresorcinol, 4-methylresorcinol (also 2,4-dihydroxytoluene), 4-ethylresorcinol, 4-propylresorcinol, 4-butylresorcinol, 4-hexylresorcinol, 4-dodecylresorcinol, 2-acetylresorcinol (also 2',6'-dihydroxyacetophenone), 2-carbomethoxyresorcinol (also methyl 2,6-dihydroxybenzoate), 1,2,3-trihydroxybenzene (also pyrogallol), 4-carbomethoxyresorcinol (also methyl 2,4-dihydroxybenzoate). Various alkanoylresorcinols can be prepared according to the method of U.S. Pat. No. 1,750,299 (Dohme) while various carboalkoxyresorcinols can be prepared according to the method U.S. Pat. No. 4,661,601 (Howell). Many methods for synthesizing substituted resorcinols suitable for use in the present disclosure are known in the chemical literature and readily available to those of ordinary skill in the chemical arts.

If no ethoxylation of the phenolic hydroxide group(s) is desired, they may be functionalized directly with polymerizable groups $R^1$ using reactants such as (meth)acryloyl chloride/pyridine or (meth)acrylic acid anhydride in the case of (meth)acrylic polymerizable groups, or using epichlorohydrin/base in the case of glycidyl groups.

Ethoxylation of phenolic hydroxyl group(s) may be achieved through conventional means such as by condensation with ethylene carbonate or ethylene oxide in the presence of hydroxide ion (e.g., from potassium hydroxide or tetrabutylammonium hydroxide) or metal salts such as potassium chloride or fluoride. Stoichiometry of the reactants will determine the degree of ethoxylation.

In some embodiments, groups such as

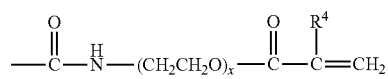

wherein R is H or methyl, x is 1 or 2 can be introduced by reaction of phenolic hydroxide on a 2,2'-diketobi[chromane] with a corresponding (meth)acrylated isocyanate represented by

Isocyanatoethyl (meth)acrylate and isocyanatoethoxyethyl (meth)acrylate are available from commercial suppliers.

In some embodiments, groups such as

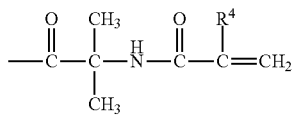

wherein $R^4$ is H or methyl can be introduced by base-catalyzed reaction of a hydroxy substituent on a 2,2'-diketobi[chromane] with a corresponding vinyl- or isopropenyldimethylazlactone, which is described, for example, in U.S. Pat. No. 5,081,197 (Heilmann et al.). 2-Vinyl-4,4-dimethylazlactone is commercially available from multiple suppliers.

Polymerizable compounds according to the present disclosure may be included in curable compositions that are free-radically polymerizable and/or epoxy compositions. They may be included in any amount, but often are present in amounts of 2-100 percent by weight, more typically 20-70 percent by weight, based on the total weight of the curable composition, with the remainder being filler and/or other monomer/oligomer compounds.

In some embodiments, the curable composition comprises a polymerizable compound according to the present disclosure (e.g., as described hereinabove) and a curative (e.g., a free radical initiator, epoxy hardener, or a catalyst for epoxy polymerization). Such curable compositions may further comprise additional free-radically polymerizable monomers, fillers, antioxidants, colorants, tougheners, and other conventional additives to free-radically polymerizable compositions.

Exemplary free-radical initiators include thermal free-radical initiators (e.g., azo compounds and peroxides) that dissociate when heated to form free-radicals, and photoinitiators that form free-radicals when exposed to actinic radiation (e.g., ultraviolet and/or visible radiation).

In some embodiments, the free-radical initiator includes one or more photoinitiators. In some embodiments, the free-radical initiator includes at least one photoinitiator active in the spectral region of 300 nanometers (nm) to 1200 nm and capable of promoting free radical polymerization and/or crosslinking of ethylenically unsaturated moieties upon exposure to light of suitable wavelength and intensity. A wide variety of such photoinitiators can be used. The photoinitiator preferably is soluble in the resin system. Preferably, the photoinitiator is sufficiently shelf stable and free of undesirable coloration to permit storage and use under typical dental operatory and laboratory conditions. Visible light photoinitiators are preferred.

One type of suitable initiator (i.e., free-radical initiator) is described in U.S. Pat. No. 5,545,676 (Palazzotto et al.), which includes a three-component or ternary photoinitiator system. This system includes an iodonium salt, e.g., a diaryliodonium salt, which can be a simple salt (e.g., containing an anion such as $Cl^-$, $Br^-$, $I^-$, or $C_2H_5SO_3$) or a metal complex salt (e.g., containing $SbF_5OH$ or $AsF_6^-$). Mixtures of iodonium salts can be used if desired. The second component in this ternary photoinitiator system is a sensitizer, which is capable of light absorption within the range of wavelengths of 400 nm to 1200 nm. The third component in this ternary photoinitiator system is an electron donor and includes amines (including aminoaldehydes and aminosilanes or other amines as described for the first initiator system), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylenediaminetetraacetic acid and salts of tetraphenylboronic acid.

Examples of sensitizers suitable for use in a ternary photoinitiator system include ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriarylmethanes, merocyanines, squarylium dyes, and pyridinium dyes. Ketones (e.g., monoketones or alpha-diketones), ketocoumarins, aminoarylketones, and p-substituted aminostyryl ketone compounds are preferred sensitizers. Examples of particularly preferred visible light sensitizers include camphorquinone, glyoxal, biacetyl, 3,3,6,6-tetramethylcyclohexanedione, 3, 3,7,7-tetramethyl-1.2-cycloheptanedione, 3,3,8,8-tetramethyl-1,2-cyclooctanedione, 3,3,18,18-tetramethyl-1,2-cyclooctadecanedione, dipivaloyl, benzil, furil, hydroxybenzil, 2,3-butanedione, 2,3-pentanedione, 2,3-hexanedione, 3,4-hexanedione, 2,3-heptanedione, 3,4 heptanedione, 2,3-octanedione, 4,5-octanedione, and 1,2-cyclohexanedione.

Yet another type of photoinitiator includes acylphosphine oxides, such as those described in European Pat. Appl. No. 0 173 567 A2 (Ying). Suitable acylphosphine oxides may be of the general formula $(R^5)_2$—P(=O)—C(=O)—$R^6$, wherein each $R^5$ is individually a hydrocarbon group, preferably an alkyl group, alicyclic group, aryl group, and aralkyl group, any of which can be substituted with a halo-, alkyl- or alkoxy-group, or the two $R^5$ groups can be joined to form a ring along with the phosphorous atom, and wherein $R^6$ is a hydrocarbon group, preferably, a S-, O-, or N-containing five- or six-membered heterocyclic group, or a —Z—C(=O)—P(=O)—$(R^5)_2$ group, wherein Z represents a divalent hydrocarbon group such as alkylene or phenylene having from 2 to 6 carbon atoms. Examples of suitable acylphosphine oxides include bis(2,4,6-trimethylbenzoyl) phenylphosphine oxide, for example. Optionally, tertiary amine reducing agents may be used in combination with an acylphosphine oxide. Illustrative tertiary amines useful in the disclosure include those described above as well as ethyl 4-(N,N-dimethylamino)benzoate and N,N-dimethylaminoethyl methacrylate.

Mono- and alpha-diketones can also be used as photoinitiators. Examples of such systems are described in U.S. Pat. No. 4,071,424 (Dart et al.).

Still another class of photoinitiators includes ionic dye-counterion complex initiators that include a borate anion and a complementary cationic dye. Borate anions useful in these photoinitiators generally can be of the formula $B(R^7)_4^-$ wherein each $R^7$ is independently an alkyl, aryl, alkaryl, allyl, aralkyl, alkenyl, alkynyl, alicyclic, and saturated or unsaturated heterocyclic groups. Cationic counterions can be cationic dyes, quaternary ammonium groups, transition metal coordination complexes, and the like.

Cationic dyes useful as counterions can be cationic methine, polymethine, triarylmethine, indoline, thiazine, xanthene, oxazine or acridine dyes. Quaternary ammonium groups useful as counterions can be trimethylcetylammonium, cetylpyridinium, and tetmmethylammonium. Other organophilic cations can include pyridinium, phosphonium, and sulfonium. Cationic transition metal coordination complexes that may be useful as counterions can be complexes of cobalt, ruthenium, osmium, zinc, iron, and iridium with ligands such as pyridine, 2,2'-bipyridine, 4,4'-dimethyl-2,2'- bipyridine, 1,10-phenanthroline, 3,4,7,8-tetramethylphenanthroline, 2,4,6-tri(2-pyridyl-s-triazine) and related ligands.

Borate salt photoinitiators are described, for example, in U.S. Pat. No. 4,772,530 (Gottschalkea et al.), U.S. Pat. No. 4,954,414 (Adair et al.), U.S. Pat. No. 4,874,450 (Gottschalkea), U.S. Pat. No. 5,055,372 (Shanklin et al.), and U.S. Pat. No. 5,057,393 (Shanklin et al.).

Visible light-induced initiators include, for example, camphorquinone combined with a suitable hydrogen donor (e.g., an amine such as those described above for the first initiator system), and optionally a diaryliodonium simple or metal complex salt, chromophore-substituted halomethyl-s-triazine, or halomethyl oxadiazole. Visible light-induced photoinitiators may include combinations of an alpha-diketone, e.g., camphorquinone with additional hydrogen donors, and optionally a diaryliodonium salt, e.g., diphenyliodonium chloride, bromide, iodide or hexafluorophosphate. Preferred ultraviolet light-induced polymerization initiators include ketones, such as benzyl and benzoin, acyloins, and acyloin ethers. Preferred ultraviolet light-induced polymerization initiators include 2,2-dimethoxy-2-phenylacetophenone and benzoin methyl ether (2-methoxy-2-phenylacetophenone).

The curative is generally present in an amount at least sufficient to provide a desired rate of hardening (e.g., polymerizing and/or crosslinking), although this is not a requirement. For a photoinitiator, this amount will be dependent in part on the light source, the thickness of the layer to be exposed to radiant energy, and the extinction coefficient of the photoinitiator. Typically, the initiator system is present in a total amount of at least 0.01 weight percent, more typically, at least 0.03 weight percent, and most typically, at least 0.05 weight percent, based on the weight of the composition. Typically, the initiator system is present in a total amount of no more than 10 weight percent, more typically, no more than weight percent, and most typically, no more than 2.5 weight percent, based on the weight of the composition.

The curable compositions may contain one or more additional free-radically polymerizable monomers. Exemplary additional free-radically polymerizable monomers include, for example, mono-, di- or poly-(meth)acrylates (i.e., acrylates and methacrylates) such as methyl (meth) acrylate, ethyl acrylate, isopropyl methacrylate, n-hexyl acrylate, 2-ethylhexyl acrylate, isobornyl acrylate, stearyl acrylate, allyl acrylate, glycerol triacrylate, ethylene glycol diacrylate, diethylene glycol diacrylate, triethylene glycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexaacrylate, tetrahydrofurfuryl (meth) acrylate, bis[1-(2-acryloxy)]-p-ethoxyphenyldimethylmethane, bis[1-(3-acryloxy-2-hydroxy)]-p-propoxyphenyldimethylmethane, ethoxylatedbisphenol A di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (typically of molecular weight 200-500); copolymerizable mixtures of acrylated monomers such as those in U.S. Pat. No. 4,652,274 (Boettcher et al.); acrylated oligomers such as those of U.S. Pat. No. 4,642,126 (Zador et al.); and vinyl compounds such as styrene, diallyl phthalate, divinyl succinate, divinyl adipate and divinyl phthalate. Other suitable additional free-radically polymerizable monomers include siloxane-functional (meth)acrylates as disclosed, for example, in PCT Pat. Publ. Nos. WO 00/38619 (Guggenberger et al.), WO 01/92271 (Weinmann et al.), WO 01/07444 (Guggenberger et al.), WO 00/42092 (Guggenberger et al.), and fluoropolymer-functional (meth) acrylates as disclosed, for example, in U.S. Pat. No. 5,076,844 (Fock et al.), U.S. Pat. No. 4,356,296 (Griffith et al.), and Eur. Pat. Appl. Nos. 0 373 384 (Wagenknecht et al.), 0 201 031 (Reiners et al.), and 0 201 778 (Reiners et al.).

Still further examples of additional free-radically polymerizable monomers include such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth) acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA).

In some embodiments, polymerizable compounds according to the present disclosure may comprise at least one epoxy group, preferably more than one epoxy group. For example, polymerizable compounds according to the present disclosure are diepoxides, often symmetric. Epoxides correspond to at least one group $R^1$ containing at least one epoxy group, often each $R^1$ group containing at least one epoxy group. Exemplary such monovalent groups $R^1$ include those represented by the formula

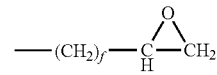

wherein f is an integer from 1 to 12. In many cases f is 1. Specific examples of various diepoxides are given in the Examples section hereinbelow.

Curable compositions according to the present disclosure may comprise at least one epoxy monomers and/or oligomers, for example. Useful epoxy monomers include, for example, alicyclic and aromatic monoepoxides and polyepoxides, and combinations thereof.

Examples of useful monoepoxides include styrene oxide, cyclohexene oxide, vinylcyclohexane oxide, allyl glycidyl ether, and glycidyl (meth)acrylate.

Examples of useful alicyclic polyepoxides include monomeric alicyclic polyepoxides, oligomeric alicyclic polyepoxides, and polymeric alicyclic polyepoxides. Exemplary alicyclic polyepoxides monomers useful in practice of the present invention include epoxycyclohexanecarboxylates such as, for example, 3,4-epoxycyclohexylmethyl 3,4-epoxycyclohexanecarboxylate and 3,4-epoxy-2-methylcyclohexylmethyl 3,4-epoxy-2-methylcyclohexanecarboxylate; diglycidyl ether of cyclohexanedimethanol; and hydrogenated bisphenol A diglycidyl ether.

Useful aromatic polyepoxides include, for example, monomeric aromatic polyepoxides, oligomeric aromatic polyepoxides, and polymeric aromatic polyepoxides.

Exemplary aromatic polyepoxides include the polyglycidyl ethers of polyhydric phenols such as bisphenol A-type resins and their derivatives; epoxy cresol-novolac resins; Bisphenol-F resins and their derivatives; epoxy phenol-novolac resins; and glycidyl esters of aromatic carboxylic acids (for example, phthalic acid diglycidyl ester, isophthalic acid diglycidyl ester, trimellitic acid triglycidyl ester, and pyromellitic acid tetraglycidyl ester), and mixtures thereof. Commercially available aromatic polyepoxides include, for example, those aromatic polyepoxides having the trade designation "EPON" (for example, EPON 828, EPON 862, EPON 1001F, EPON DPL-862, and EPON HPT-1079) available from Hexion Specialty Chemicals, Columbus, Ohio; and aromatic polyepoxides having the trade designations DER and DEN (for example, DEN 438, and DEN 439), and QUATREX as available from Dow Chemical Co.

An effective amount of thermal curative for the at least one epoxy monomer is included in the curable composition such that it can be sufficiently cured to develop a C-stage. Hence, the term "effective amount of thermal curative" refers to at least a minimum quantity. The precise amount will necessarily vary due to formulation and curing variables, but it is typically 10 percent by weight or less based on the total weight of the curable composition.

Useful thermal curatives for the polyepoxide(s) include acid curatives and base curatives. Examples of useful curing agents include boron trifluoride complexes such as, for example, $BF_3Et_2O$ and $BF_3H_2NC_2H_4OH$; polyamines such as, for example, bis(4-aminophenyl)sulfone, bis(4-aminophenyl)ether, and 2,2-bis(4-aminophenyl)propane; aliphatic and aromatic tertiary amines such as, for example, dimethylaminopropylamine; fluorenediamines; imidazoles such as, for example, methylimidazole and 2,4-diamino-6-(2'-methylimidazolyl-(1'))-ethyl-s-triazine hexakis(imidazole)nickel phthalate); hydrazines such as, for example, adipohydrazine; guanidines, such as, for example, tetramethylguanidine and dicyandiamide (cyanoguanidine, also commonly known as DiCy); and combinations thereof.

Curable compositions can optionally further comprise one or more fillers (i.e., a filler system). Many conventional fillers are suitable (e.g., silica, zirconia, alumina, talc, carbon black). In some embodiments, Typically, the filler system includes one or more conventional materials suitable for incorporation in compositions used for medical applications, for example, fillers currently used in medical/dental restorative compositions. Thus, the filler systems used in the compositions of the present disclosure are incorporated into the resin systems.

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles, in particular the uniformity of the shape.

Preferred particulate filler is finely divided and has an average particle size (typically, diameter) of less than 10 micrometers (i.e., microns).

Preferred micron-size particulate filler has an average particle size of at least 0.2 micron up to 1 micrometer. Nanoscopic particles have an average primary particle size of less than 200 nm (0.2 micron). The filler can have a unimodal or polymodal (e.g., bimodal) particle size distribution.

Micron-size particles are very effective for improving post-cure wear properties. In contrast, nanoscopic fillers are commonly used as viscosity and thixotropy modifiers. Due to their small size, high surface area, and associated hydrogen bonding, these materials are known to assemble into aggregated networks. Materials of this type ("nanoscopic" materials) have average primary particle sizes (i.e., the largest dimension, e.g., diameter, of unaggregated material) of no greater than 1000 nanometers (inn). Typically, the nanoscopic particulate material has an average primary particle size of at least 2 nanometers (nm), and typically at least 7 nm. Typically, the nanoscopic particulate material has an average primary particle size of no greater than 50 nm, and more typically no greater than 20 nm in size. The average surface area of such a filler is typically at least 20 square meters per gram ($m^2/g$), more typically, at least 50 $m^2/g$, and most typically, at least 100 $m^2/g$.

The filler system can include an inorganic material. It can also include a crosslinked organic material that is insoluble in the polymerizable resin and is optionally filled with inorganic filler. The filler system is typically generally non-toxic and suitable for use in the mouth.

Suitable fillers can be radiopaque, radiolucent, or nonradiopaque. Fillers as used in dental applications are typically ceramic in nature. Examples of suitable inorganic fillers are naturally occurring or synthetic materials such as quartz, nitrides (e.g., silicon nitride), glasses derived from, for example Ce, Sb, Sn, Zr, Sr, Ba, or Al, colloidal silica, feldspar, borosilicate glass, kaolin, talc, titania, and zinc glass, zirconia-silica fillers; and low Mohs hardness fillers such as those described in U.S. Pat. No. 4,695,251 (Randklev). Examples of suitable organic filler particles include filled or unfilled pulverized polycarbonates, polyepoxides, and the like. Preferred filler particles are quartz, submicron silica, and non-vitreous microparticles of the type described in U.S. Pat. No. 4,503,169 (Randklev). Mixtures of these fillers can also be used, as well as combination fillers made from organic and inorganic materials.

Optionally, the surface of the filler particles may be treated with a surface treatment, such as a silane-coupling agent, in order to enhance the bond between the filler system and the resin system. The coupling agent may be functionalized with reactive curing groups, such as acrylates, methacrylates, and the like.

The filler particles used to impart a noncovalent structure can be composed of silica, alumina, zirconia, titania, or mixtures of these materials with each other or with carbon. In their synthesized state, these materials are commonly hydrophilic, due to the presence of surface hydroxyl groups. However, the materials may also be modified by treatment with appropriate agents, such as alkyl silanes, in order to modify this character. For example, the surface of a filler particle may be rendered neutral, hydrophobic, or reactive, depending on the desired properties. Fumed silica is a preferred compound for imparting self-supporting character, due to its low cost, commercial availability, and wide range of available surface character.

Other suitable fillers are disclosed in U.S. Pat. No. 6,387,981 (Zhang et al.) and U.S. Pat. No. 6,572,693 (Wu et al.) as well as International Publication Nos. WO 01/30305 (Zhang et al.), WO 01/30306 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. Pat. No. 7,649,029 (Budd et al.) and U.S. Pat. No. 7,156,911 (Bui et al.).

Typically, the total amount of filler system is greater than 50 weight percent, more typically, greater than 60 weight percent, and most typically, greater than 70 weight percent, based on the total weight of the composition. If the filler system includes fibers, the fibers are present in an amount of less than 20 weight percent, based on the total weight of the composition. Typically, the total amount of filler system is no more than 95 weight percent, and more typically, no more than 80 weight percent, based on the total weight of the composition.

The curable composition may additionally include optional agents such as, for example, colorants (e.g., pigments or dyes conventionally used for shade adjustment), flavoring agents, surfactants, medicaments, stabilizers (e.g., butylated hydroxytoluene (BHT)), viscosity modifiers, diluting agents, flow control additives, thixotropic agents, antimicrobials, and polymeric thickeners. Various combinations of these optional additives can be used if desired. Such agents may optionally include reactive functionality so that they will be copolymerized with the resin.

Typically, the total amount of optional additives is no more than 5.0 weight percent, more typically, no more than about 2.5 weight percent, and most typically, no more than 1.5 weight percent, based on the total weight of the curable composition.

Curing may be accomplished by any suitable method. Examples include heating (e.g., oven, microwave heating, radiant heating, radiofrequency heating, or using a hot plate or roll) and exposure to actinic radiation (e.g., ultraviolet and/or visible electromagnetic radiation) using an appropriate light source, preferably in an inert atmosphere. Examples include mercury lamps (e.g., low, medium, and or high pressure mercury lamps), xenon flashlamps, light emitting diode (LED) arrays, microwave-driven lamps, and lasers. If heated, at least minimum heating temperature capable of decomposing the thermal free-radical initiator may be used (e.g., 60° C., 80° C., 100° C., or even higher). Selection of suitable heating and/or electromagnetic radiation exposure conditions is within the capabilities of those having ordinary skill in the art.

Curing of the curable composition may be partial or complete and results in an at least partially cured composition. In many cases, partial curing will be sufficient to achieve acceptable material properties for a given intended use.

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight.

Column chromatography purification of compounds was conducted using an ISOLARA HPFC system (an automated high-performance flash chromatography purification instrument available from Biotage, Inc, Charlottesville, Virginia). The eluent used for each purification is described in the examples.

Proton nuclear magnetic resonance ($^1$H NMR, $^{13}$C NMR) analyses were conducted using a BRUKER A500 NMR spectrometer (Bruker Corporation, Billerica, Massachusetts).

Resorcinol, 4-ethylresorcinol, anhydrous citric acid, phosphorous pentoxide, methanesulfonic acid, ethylene carbonate, 1,8-diazabicyclo[5.4.0]undec-7-ene (DBU), dibutyltin dilaurate (DBTDL), epichlorohydrin, dioxane, tetrabutylammonium bromide, diethylenetriamine, diphenyliodonium hexafluorophosphate (DPIHPF) and dimethyl acetonedicarboxylate were obtained from Alfa Aesar, Ward Hill, Massachusetts.

4-Chlororesorcinol was obtained from Oakwood Chemical, Estill, South Carolina.

Isocyanatoethoxyethyl methacrylate (IEEMA), isocyanatoethyl methacrylate (IEMA) and isocyanatoethyl acrylate (IEA) were obtained from Showa Denko, Europe GmbH, Munich, Germany.

Sulfuric acid, acetone, chloroform, methanol, acetonitrile, ethyl acetate, tetrahydrofuran, dichloromethane, magnesium sulfate and potassium chloride were obtained from EMD Millipore, Burlington, Massachusetts.

Urethane dimethacrylate (UDMA) was obtained from Esstech Inc., Essington, Pennsylvania.

m-Xylylenediamine was obtained from Fisher Scientific, Pittsburgh, Pennsylvania.

1,12-dodecanediol dimethacrylate (DDDMA) was obtained from Sartomer Company, Exton, Pennsylvania.

Benzotriazole (BZT) was obtained from Ciba Inc., Tarrytown, New Jersey.

Ethyl 4-(dimethylamino)benzoate (EDMAB), azobisisobutyronitrile (AIBN), camphorquinone (CPQ), butylated hydroxytoluene (BHT), 2-ethylhexyl acrylate, and isobornyl acrylate are available from the Sigma-Aldrich Company, St. Louis, Missouri.

Ytterbium fluoride (100 nm) was obtained from Sukgyung AT Company, Ltd, Gyeonggi-do, Korea.

Vinyl-4,4-dimethylazlactone is available from Isochem North America, LLC, Syosset, New York.

ERGP-IEM, AFM1, and Filtek Bulk Fill Posterior Restorative (FBFPR) were obtained from 3M Company, St Paul, MN.

Yoga surface-treated LE clusters were prepared as described in U.S. Pat. No. 8,647,510 (Kolb et al.).

Crystal surface-treated nanozirconia filler was prepared as described in U.S. Pat. No. 8,647,510 (Kolb et al.).

Supreme surface-treated silica filler was prepared as described in U.S. Pat. No. 6,572,693 (Wu et al.).

Stress Test Method

To measure stress development during the curing process, a slot was machined into a rectangular 8×10×15 mm aluminum block, generally as shown in FIG. 1 of U.S. Pat. No. 9,320,685 (Moser et al.). The slot was 8 mm long, 4 mm deep, and 4 mm across, and was located 2 mm from an edge, thus forming a 2 mm wide aluminum cusp adjacent to a 2 mm wide cavity containing dental compositions being tested.

A linear variable displacement transducer (Model GT 1000, used with an E309 analog amplifier, both from RDP Electronics, United Kingdom) was positioned as shown to measure the displacement of the cusp tip as the dental composition photocured at room temperature. Prior to testing, the slot in the aluminum block was sandblasted using Rocatec Plus Special Surface Coating Blasting Material (3M ESPE), treated with RelyX Ceramic Primer (3M ESPE), and finally treated with a dental adhesive, Scotchbond Universal (3M). The slot was fully packed with the mixtures shown Table 2, which equaled approximately 100 mg of material. The material was irradiated for 1 minute with a dental curing light (Elipar S-10, 3M) positioned almost in contact (<1 mm) with the material in the slot, then the displacement of the cusp in microns was recorded 9 minutes after the lamp was extinguished.

Depth of Cure Test Method

The depth of cure was determined by filling a 10 millimeter stainless steel mold cavity with the composite, covering the top and bottom of the mold with sheets of polyester film, pressing the sheets to provide a leveled composition surface, placing the filled mold on a white background surface, irradiating the dental composition for 20 seconds using a dental curing light (3M Dental Products Curing Light 2500 or 3M ESPE Elipar FreeLight2, 3M ESPE Dental Products) positioned almost in contact (<1 mm) with the material in the slot, separating the polyester films from each side of the mold, gently removing (by scraping) materials from the bottom of the sample (i.e., the side that was not irradiated with the dental curing light), and measuring the thickness of the remaining material in the mold. The reported depths are the measured cured thickness in millimeters divided by two.

Diametral Tensile Strength Test Method

Diametral tensile strength was measured per the following procedure. The uncured composite sample was injected into a glass tube that was about 30 mm long with a 4 mm inside diameter. It was filled about ½ full and capped with silicone rubber plugs. The tube was compressed axially at approximately 3 kg/cm² pressure for 5 minutes. While still under pressure, the sample was then light cured for 60 seconds by exposure to a dental curing light with a radiant exitance of greater than 1000 mW/cm². The tube was rotated as it cured to ensure equal exposure. A Buehler Iso Met 4000 (Illinois Tool Works, Lake Bluff, Illinois) saw was then used to section disks about 2 mm thick from the tube. The resulting disks were stored in distilled water at 37° C. for about 24 hours prior to testing. Measurements were carried out using an appropriate materials test frame (e.g.: Instron 5966, Instron Corp., Canton, Massachusetts) with a 10 kilonewton load cell at a crosshead speed of 1 mm per minute. Diametral tensile strength was calculated as described in Craig's Restorative Dental Materials, (Ronald L. Sakaguchi and John M. Powers, "Testing of Dental Materials and Biomechanics" in Craig's Restorative Dental Materials, 13th ed., Elsevier, 2012, p. 86).

Preparative Example 1

Preparation of 7, 7'-Dihydroxy-4,4'-spirobi[chromane]-2,2'-dione

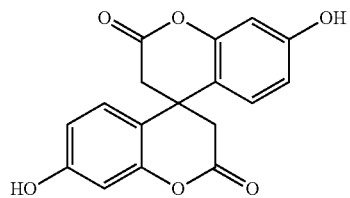 [SMILES: O=C1CC2(CC(=O)Oc3cc(O)ccc32)c2ccc(O)cc2O1]

7,7'-Dihydroxy-4,4'-spirobi[chromane]-2,2'-dione was prepared by a modification of the procedure described in Dixit et. al. (J. Ind. Chem. Soc. 1945, 22, 207-213). Anhydrous citric acid (50.5 g, 260 mmol) was mixed with concentrated sulfuric acid (90 mL) in a 500 mL RB flask under nitrogen and heated to 55° C. with stirring. Heating was continued until bubbling had largely ceased (~3 hours), and then the solution was allowed to cool. The yellow solution was poured carefully onto 152 g ice, left to stand for a few minutes, then transferred to a refrigerator and left overnight. The suspension was filtered under vacuum, and the solid dried on a porous plate yielding 25.45 g of white crystals. This solid (acetonedicarboxylic acid) was used without further purification in the next step.

Resorcinol (39.99 g, 262 mmol) was ground together with acetonedicarboxylic acid (20.53 g, 141 mmol). The mixture was added to a 1-L jar and phosphorus pentoxide (14.95 g, 05 mmol) was added in small portions with constant stirring. The solid orange product was stirred in deionized water (~500 mL) at RT overnight. The resultant suspension was filtered under vacuum to yield an off-white solid. The solid was stirred sequentially three times with saturated sodium bicarbonate (500 mL) followed by water (500 mL) and dried on the filter, yielding 21.10 g of 7,7'-dihydroxy-4,4'-spirobi [chromane]-2,2'-dione. $^1$H NMR (acetone-$d_6$, 500 MHz) δ 8.97 (s, 2H), 6.87 (d, J=8.3 Hz, 2H), 6.66 (dd, J=8.3, 2.7 Hz, 2H), 6.64 (d, J=2.5 Hz, 2H), 3.25 (d, J=15.4 Hz, 2H), 3.01 (d, J=15.4 Hz, 2H). $^{13}$C NMR (acetone-$d_6$, 126 MHz) δ 166.1, 158.9, 152.6, 127.0, 117.1, 112.5, 104.5, 40.1, 38.4.

Preparative Example 2

Preparation of 6,6'-diethyl-7, 7'-dihydroxy-4,4'-spirobi[chromane]-2,2'-dione

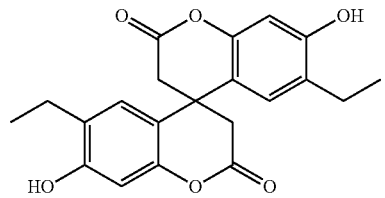 [SMILES: CCc1cc2c(cc1O)OC(=O)CC21CC(=O)Oc2cc(O)c(CC)cc21]

4-Ethylresorcinol (20.07 g, 144.8 mmol) was ground together with acetonedicarboxylic acid (10.05, 68.79 mmol). The mixture was added to a 100-mL jar and phosphorus pentoxide (10 g, 69 mmol) was added in small portions with constant stirring. Once the reaction mixture had cooled, it was stirred in deionized water (~700 mL) at RT overnight. The suspension was filtered under vacuum to yield an off-white solid. The solid was stirred with saturated sodium bicarbonate (700 mL) followed by water (500 mL) and dried on the filter yielding 7.43 g of 6,6'-diethyl-7,7'-dihydroxy-4,4'-spirobi[chromane]-2,2'-dione. 1H NMR (500 MHz, acetone-$d_6$) δ 8.87 (b, 2H), 6.80 (s, 2H), 6.64 (s, 2H), 3.23 (d, J=15.4 Hz, 2H), 2.96 (d, J=15.2 Hz, 2H), 2.54 (dq, J=1.5, 7.6 Hz, 4H), 1.09 (t, J=7.5 Hz, 6H). $^{13}$C NMR (126 MHz, acetone-$d_6$) δ 166.4, 156.1, 150.4, 127.8, 126.4, 116.9, 103.9, 40.9, 38.6, 23.0, 14.1.

Preparative Example 3

Preparation of 6,6'-dichloro-7, 7'-dihydroxy-4,4'-spirobi[chromane]-2,2'-dione

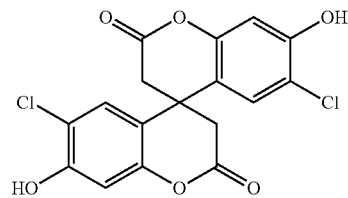 [SMILES: O=C1CC2(CC(=O)Oc3cc(O)c(Cl)cc32)c2cc(Cl)c(O)cc2O1]

Dimethyl acetonedicarboxylate (0.5 mL, 3.40 mmol) was mixed with 4-chlororesorcinol (2.5 g, 17.3 mmol), stirred and cooled in an ice bath. Methanesulfonic acid (10 mL) was added dropwise over 20 minutes. The reaction solution was left stirring and allowed to warm up overnight. The suspension was added dropwise to 600 mL deionized water with vigorous stirring. The suspension was stirred for a further hour, then filtered, dried on the filter with flowing air, and in a vacuum oven overnight. The solid was then stirred in ice-cold acetonitrile (10 mL), filtered, and dried under vacuum to yield a tan solid (1.74 g). This was purified by column chromatography using 50 g silica gel and eluting with 1%-8% MeOH/CHCl$_3$ to give 1.25 g of 6,6'-dichloro-7,7'-dihydroxy-4,4'-spirobi[chromane]-2,2'-dione. $^1$H NMR (500 MHz, acetone-d$_6$) δ 9.52 (s, 2H), 7.06 (s, 2H), 6.87 (s, 2H), 3.37 (d, J=15.4 Hz, 2H), 3.13 (d, J=15.4 Hz, 2H). $^{13}$C NMR (126 MHz, acetone-d$_6$) δ 164.8, 153.8, 150.5, 126.4, 117.5, 116.4, 105.4, 39.4, 38.0.

Preparative Example 4

Preparation of 7,7'-bis(2-hydroxyethoxy)-4,4'-spirobi[chromane]-2,2'-dione

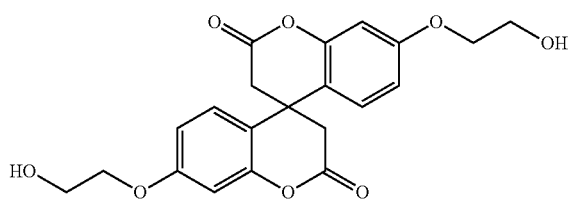 [SMILES: O=C1CC2(CC(=O)Oc3cc(OCCO)ccc32)c2ccc(OCCO)cc2O1]

Ethylene carbonate (3.40 g, 38.6 mmol) was melted with a hot air gun and added by pipet to 7,7'-dihydroxy-4,4'-spirobi[chromane]-2,2'-dione prepared hereinabove (4.63 g=14.8 mmol) in a 100-mL jar and the solid stirred to mix. The jar was heated to 180° C. for one hour, then potassium chloride (15.4 mg, 0.21 mmol) was added, the mixture stirred briefly, and heating continued for seven hours. The reaction mixture was left to cool overnight and filtered to isolate solids, which were washed on the filter with water and dried under vacuum overnight. The product was purified by column chromatography (SiO$_2$, 3-20% methanol/CHCl$_3$). $^1$H NMR (500 MHz, acetone-d$_6$) δ 6.95 (d, J=9.5 Hz, 2H), 6.78 (m, 4H), 4.11 (t, J=4.8 Hz, 4H), 3.87 (t, J=4.8 Hz, 4H), 3.29 (d, J=15.4 Hz, 2H), 3.05 (d, J=15.4 Hz, 2H). $^{13}$C NMR (126 MHz, acetone-d$_6$) δ 166.0, 160.7, 152.6, 126.9, 118.0, 111.8, 103.7, 70.6, 60.6, 40.4, 38.5.

Preparative Example 5

Preparation of 6,6'-diethyl-7, 7'-bis(2-hydroxyethoxy)-4,4'-spirobi[chromane]-2,2'-dione

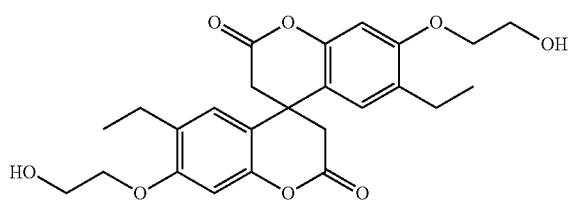 [SMILES: CCc1cc2c(cc1OCCO)OC(=O)CC21CC(=O)Oc2cc(OCCO)c(CC)cc21]

Ethylene carbonate (2.67 g, 30.3 mmol) was melted with a hot air gun and added by pipet to 6,6'-diethyl-7,7'-dihydroxy-4,4'-spirobi[chromane]-2,2'-dione prepared above (5.00 g, 13.6 mmol) in a 100-mL jar and the solid stirred to mix. The jar was heated to 180° C. for five minutes, then potassium chloride (46 mg, 0.61 mmol) was added, the mixture stirred briefly, and heating continued overnight. The product was dissolved in acetone, the bulk of the acetone removed under vacuum, then water was added, and the rest of the solvent removed. It was then triturated in deionized water for one hour and dried under vacuum overnight to yield 5.79 g of 6,6'-diethyl-7,7'-bis(2-hydroxyethoxy)-4,4'-spirobi[chromane]-2,2'-dione, which was further purified by column chromatography (SiO$_2$, 5-20% acetone/CHCl$_3$). $^1$H NMR (500 MHz, acetone-d$_6$) δ 6.83 (s, 2H), 6.79 (s, 2H), 4.15 (m, 4H), 4.02 (t, J=5.7 Hz, 2H), 3.92 (m, 4H), 3.26 (d, J=15.4 Hz, 2H), 3.00 (d, J=15.4 Hz, 2H), 2.55 (dq, J=2.0, 7.8 Hz, 4H), 1.07 (t, J=7.6 Hz, 6H). $^{13}$C NMR (126 MHz, acetone-d$_6$) δ 166.2, 157.9, 150.7, 129.6, 126.0, 117.2, 101.2, 70.7, 60.8, 40.7, 38.7, 23.1, 14.1.

Preparative Example 6

Preparation of 6,6'-dichloro-7, 7'-bis(2-hydroxyethoxy)-4,4'-spirobi[chromane]-2, 2'-dione

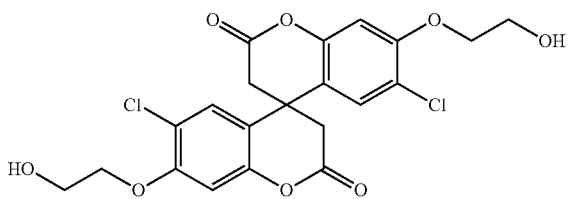 [SMILES: O=C1CC2(CC(=O)Oc3cc(OCCO)c(Cl)cc32)c2cc(Cl)c(OCCO)cc2O1]

Ethylene carbonate (4.99 g, 56.7 mmol) was mixed with 6,6'-dichloro-7,7'-dihydroxy-4,4'-spirobi[chromane]-2,2'-dione prepared above (10.02 g, 26.3 mmol) and potassium chloride (250 mg, 3.3 mmol) in a 100 mL glass bottle under nitrogen, heated to 160° C. and left overnight with stirring. The product was allowed to cool and then a 3 g quantity was purified by column chromatography using 100 g of silica gel and eluting with 2.4%-20% acetone/CHCl$_3$ to give 0.8 g of 6,6'-dichloro-7,7'-bis(2-hydroxyethoxy)-4,4'-spirobi[chromane]-2,2'-dione. $^1$H NMR (500 MHz, acetone-d$_6$) δ 7.07 (s, 2H), 7.05 (s, 2H), 4.25 (t, J=4.7 Hz, 4H), 4.17 (t, J=5.7 Hz, 2H), 3.94 (dd, J=5.5, 4.4 Hz, 4H), 3.38 (d, J=15.4 Hz, 2H), 3.15 (d, J=15.4 Hz, 2H). $^{13}$C NMR (500 MHz, acetone-d$_6$) δ 165.4, 155.9, 151.2, 126.9, 118.4, 118.1, 103.6, 71.7, 60.5, 39.8, 38.6.

Example 1

Preparation of 2-[2-[2-[[7'-[2-[2-[2-(2-methylprop-2-enoyloxy)ethoxy]ethylcarbamoyloxy]ethoxy]-2,2'-dioxo-4,4'-spirobi[chromane]-7-yl]oxy]ethoxycarbonylamino]ethoxy]ethyl 2-methylprop-2-enoate

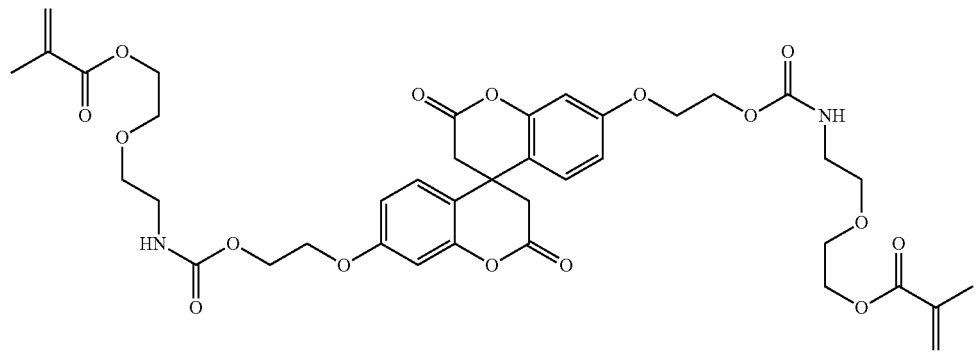 [SMILES: C=C(C)C(=O)OCCOCCNC(=O)OCCOc1ccc2c(c1)OC(=O)CC21CC(=O)Oc2cc(OCCOC(=O)NCCOCCOC(=O)C(=C)C)ccc21]

7,7'-Bis(2-hydroxyethoxy)-4,4'-spirobi[chromane]-2,2'-dione prepared above (4.57 g) was dissolved in ethyl acetate (15 mL) and isocyanatoethoxyethyl methacrylate (IEEMA, 3.50 g) was added. The solution was heated to 60° C. and dibutyltin dilaurate (DBTDL, 10 μL) added. After 1.5 hours the reaction was allowed to cool and left to stir at RT overnight. The solvent was removed under reduced pressure, yielding 2-[2-[2-[[7'-[2-[2-[2-(2-methylprop-2-enoyloxy)ethoxy]ethylcarbamoyloxy]ethoxy]-2,2'-dioxo-4,4'-spirobi[chromane]-7-yl]oxy]ethoxycarbonylamino]ethoxy]ethyl 2-methylprop-2-enoate as a colorless oil. $^1$H NMR (500 MHz, acetone-$d_6$) δ 6.97 (d, J=8.2 Hz, 2H), 6.79 (m, 4H), 6.32 (br s, 2H), 6.07 (s, 2H), 5.61 (t, J=1.6 Hz, 2H), 4.35 (m, 4H), 4.24 (m, 8H), 3.71 (m, 4H), 3.56 (t, J=5.6 Hz, 4H), 3.29 (m, 6H), 3.06 (d, J=15.4 Hz, 2H), 1.96 (s, 6H). $^{13}$C NMR (126 MHz, acetone-$d_6$) δ 166.9, 165.9, 160.2, 156.5, 152.6, 136.8, 127.0, 125.3, 118.3, 111.8, 103.8, 69.9, 68.8, 67.3, 64.0, 62.8, 40.9, 40.4, 38.5, 17.9.

Example 2

Preparation of 2-[2-[[7'-[2-[2-(2-methylprop-2-enoyloxy)ethylcarbamoyloxy]ethoxy]-2,2'-dioxo-4,4'-spirobi[chromane]-7-yl]oxy]ethoxycarbonylamino] ethyl 2-methylprop-2-enoate

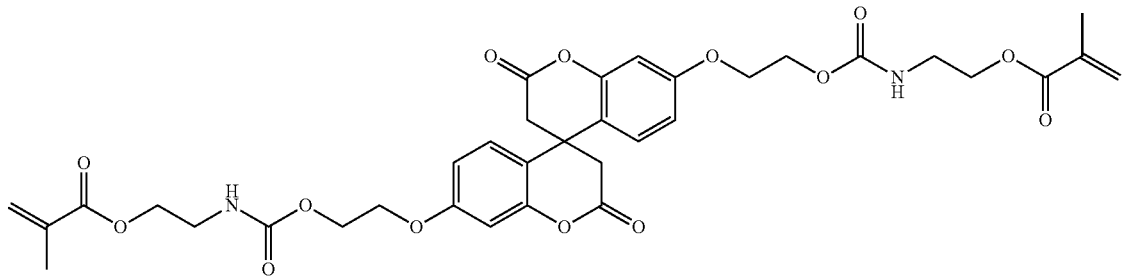 [SMILES: C=C(C)C(=O)OCCNC(=O)OCCOc1ccc2c(c1)OC(=O)CC21CC(=O)Oc2cc(OCCOC(=O)NCCOC(=O)C(=C)C)ccc21]

7,7'-Bis(2-hydroxyethoxy)-4,4'-spirobi[chromane]-2,2'-dione prepared above (0.501 g, 1.25 mmol) was dissolved in ethyl acetate (2 mL) with isocyanatoethyl methacrylate (IEMA) (0.3935 g, 2.54 mmol). DBTDL (10 μL, 0.068 mmol) was added and the solution was heated to 60° C. for one hour. It was then left to stir at RT overnight. The solvent was removed under reduced pressure, and the product purified by column chromatography (SiO$_2$, 5-20% acetone/ CHCl$_3$). $^1$H NMR (500 MHz, acetone-$d_6$) δ 6.96 (d, J=9.1 Hz, 2H), 6.80 (m, 4H), 6.61 (br s, 2H), 6.08 (s, 2H), 5.59 (m, 2H), 4.36 (m, 4H), 4.24 (m, 4H), 4.19 (t, J=5.5 Hz, 4H), 3.45 (m, 4H), 3.31 (d, J=15.4 Hz, 2H), 3.08 (d, J=15.4 Hz, 2H), 1.89 (s, 6H). $^{13}$C NMR (126 MHz, acetone-$d_6$) δ 166.9, 165.9, 160.2, 156.7, 152.6, 136.8, 127.0, 125.4, 118.3, 111.8, 103.8, 67.3, 63.8, 62.9, 40.4, 40.1, 38.5, 17.9.

Example 3

Preparation of 2-[2-[[2,2'-dioxo-7'-[2-(2-prop-2-enoyloxyethylcarbamoyloxy)ethoxy]-4,4'-spirobi[chromane]-7-yl]oxy]ethoxycarbonylamino]ethyl prop-2-enoate

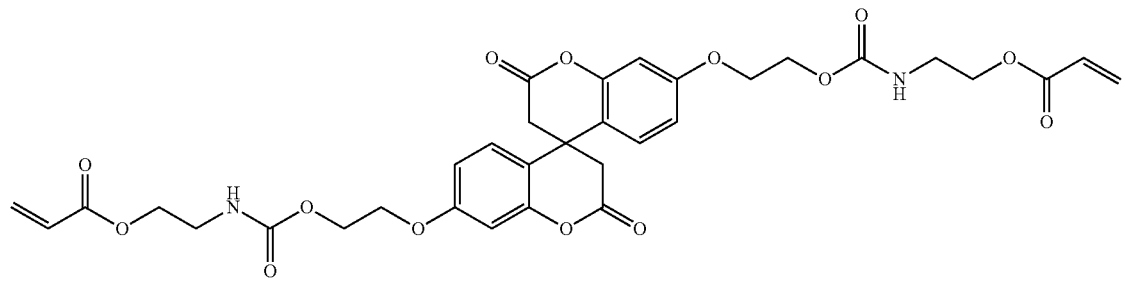 [SMILES: C=CC(=O)OCCNC(=O)OCCOc1ccc2c(c1)OC(=O)CC21CC(=O)Oc2cc(OCCOC(=O)NCCOC(=O)C=C)ccc21]

7,7'-Bis(2-hydroxyethoxy)-4,4'-spirobi[chromane]-2,2'-dione prepared above (0.498 g, 1.24 mmol) was dissolved in ethyl acetate (2 mL) with isocyanatoethyl acrylate (IEA) (0.360 g, 2.57 mmol). DBTDL (10 µL, 0.068 mmol) was added and the solution was heated to 60° C. for one hour. It was then left to stir at RT overnight. The solvent was removed under reduced pressure, and the product purified by column chromatography (SiO$_2$, 5-20% acetone/CHCl$_3$). $^1$H NMR (500 MHz, acetone-d$_6$) δ 6.97 (d, J=9.3 Hz, 2H), 6.79 (m, 4H), 6.61 (br s, 2H), 6.36 (dd, J=17.4, 1.3 Hz, 2H), 6.13 (dd, J=17.4, 10.3 Hz, 2H), 5.88 (dd, J=10.5, 1.5 Hz, 2H), 4.37 (m, 4H), 4.24 (m, 4H), 4.20 (t, J=5.5 Hz, 4H), 3.44 (m, 4H), 3.30 (d, J=15.4 Hz, 2H), 3.06 (d, J=15.4 Hz, 2H). $^{13}$C NMR (126 MHz, acetone-d$_6$) δ 165.9, 165.8, 160.2, 156.6, 152.6, 130.8, 128.8, 127.0, 118.3, 111.8, 103.8, 67.2, 63.5, 62.9, 40.3, 40.1, 38.5.

Example 4

Preparation of 2-[[7'-[2-[2-methyl-2-(prop-2-enoylamino)propanoyl]oxyethoxy]-2,2'-dioxo-4,4'-spirobi[chromane]-7-yl]oxy]ethyl 2-methyl-2-(prop-2-enoylamino)propanoate

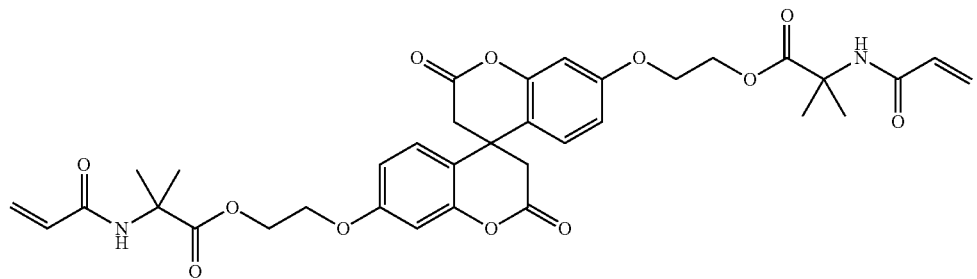 [SMILES: C=CC(=O)NC(C)(C)C(=O)OCCOc1ccc2c(c1)OC(=O)CC21CC(=O)Oc2cc(OCCOC(=O)C(C)(C)NC(=O)C=C)ccc21]

7,7'-Bis(2-hydroxyethoxy)-4,4'-spirobi[chromane]-2,2'-dione prepared above (0.501 g, 1.25 mmol) was dissolved in ethyl acetate (2 mL) with vinyl-4,4-dimethylazlactone (VDM, 0.350 g, 2.57 mmol). 1,8-Diazabicyclo[5.4.0]undec-7-ene (DBU) (5 µL, 0.068 mmol) was added and the solution was heated to 60° C. overnight. Another 5 µL DBU was added and heating continued for a further day. Solvent was removed under reduced pressure and the product purified by column chromatography (SiO$_2$, 5-20% acetone/CHCl$_3$). $^1$H NMR (500 MHz, acetone-d$_6$) δ 7.62 (br s, 2H), 6.96 (d, J=9.3 Hz, 2H), 6.78 (m, 4H), 6.21 (dd, J=17.2, 10.3 Hz, 2H), 6.07 (dd, J=17.2, 2.1 Hz, 2H), 5.50 (dd, J=10.3, 2.2 Hz, 2H), 4.42 (m, 4H), 4.25 (m, 4H), 3.30 (d, J=15.4 Hz, 2H), 3.06 (d, J=15.4 Hz, 2H), 1.46 (s, 12H). $^{13}$C NMR (216 MHz, acetone-d$_6$) δ: 174.0, 166.0, 164.5, 160.3, 152.6, 131.5, 126.9, 125.5, 118.3, 111.9, 104.0, 66.9, 63.1, 55.8, 40.4, 38.5, 24.8

Example 5

Preparation of 2-[2-[2-[[6,6'-diethyl-7'-[2-[2-[2-(2-methylprop-2-enoyloxy)ethoxy]ethylcarbamoyloxy]-ethoxy]-2,2'-dioxo-4,4'-spirobi[chromane]-7-yl]oxy]ethoxycarbonylamino]ethoxy]ethyl-2-methylprop-2-enoate

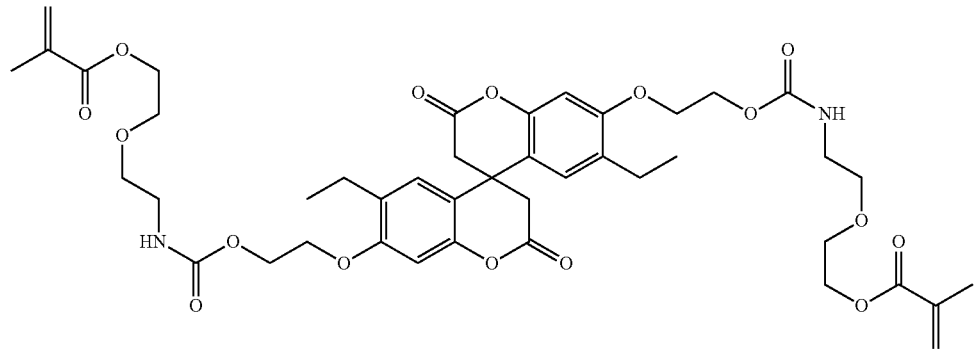 [SMILES: C=C(C)C(=O)OCCOCCNC(=O)OCCOc1cc2c(cc1CC)C1(CC(=O)O2)CC(=O)Oc2cc(OCCOC(=O)NCCOCCOC(=O)C(=C)C)c(CC)cc21]

6,6'-Diethyl-7,7'-bis(2-hydroxyethoxy)-4,4'-spirobi[chromane]-2,2'-dione prepared above (1.03 g, 2.28 mmol) was stirred in tetrahydrofuran (THF) (10 mL), filtered and then IEEMA (0.495 g) was added. The solution was heated to 60° C. and dibutyltin dilaurate (DBTDL, 10 μL) added. After one hour the reaction was allowed to cool and the solvent was removed under vacuum overnight. The product was purified by column chromatography (SiO$_2$, 5-20% acetone/CHCl$_3$) $^1$H NMR (500 MHz, acetone-d$_6$) δ 6.83 (s, 2H), 6.80 (s, 2H), 6.31 (br s, 2H), 6.05 (s, 2H), 5.61 (t, J=1.6 Hz, 2H), 4.41 (m, 4H), 4.24 (m, 8H), 3.70 (t, J=4.7 Hz, 4H), 3.56 (t, J=5.7 Hz, 4H), 3.27 (m, 6H), 3.06 (d, J=15.4 Hz, 2H), 2.53 (m, 4H), 1.89 (s, 6H), 1.05 (t, J=7.5 Hz, 6H). $^{13}$C NMR (126 MHz, acetone-d$_6$) δ 166.9, 166.2, 157.5, 156.6, 150.7, 136.8, 129.6, 126.1, 125.3, 117.5, 101.3, 69.9, 68.8, 67.5, 64.0, 62.8, 40.9, 40.7, 38.7, 23.2, 17.9, 14.1.

Example 6

Preparation of 2-[2-[[6,6'-diethyl-7'-[2-[2-(2-methylprop-2-enoyloxy)ethylcarbamoyloxy]ethoxy]-2,2'-dioxo-4,4'-spirobi[chromane]-7-yl]oxy]ethoxycarbonylamino]ethyl 2-methylprop-2-enoate

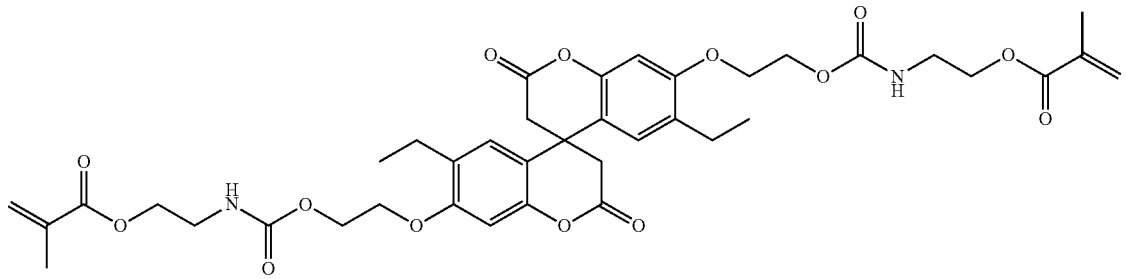 [SMILES: C=C(C)C(=O)OCCNC(=O)OCCOc1cc2c(cc1CC)C1(CC(=O)O2)CC(=O)Oc2cc(OCCOC(=O)NCCOC(=O)C(=C)C)c(CC)cc21]

6,6'-Diethyl-7,7'-bis(2-hydroxyethoxy)-4,4'-spirobi[chromane]-2,2'-dione prepared above (0.98 g, 2.15 mmol) was stirred in THF (10 mL), filtered and then IEMA (0.55 mL, 3.90 mmol) was added. The solution was heated to 60° C. and DBTDL (11 IL, 0.018 mmol) added. After one hour the reaction was allowed to cool and the solvent removed under vacuum overnight. Product was purified by column chromatography (SiO$_2$, 5-20% acetone/chloroform). $^1$H NMR (acetone-d$_6$, 500 MHz) δ 6.84 (s, 2H), 6.80 (s, 2H), 6.61 (br, 2H), 6.07 (s, 2H), 5.59 (s, 2H), 4.42 (m, 4H), 4.27 (m, 4H), 4.19 (t, J=5.5 Hz, 4H), 3.45 (q, J=5.7 Hz, 4H), 3.27 (d, J=15.4 Hz, 2H), 3.01 (d, J=15.4 Hz, 2H), 2.52 (m, 4H), 1.88 (s, 6H), 1.06 (t, J=7.5 Hz, 6H). $^{13}$C NMR (acetone-d$_6$, 126 MHz) δ 166.9, 166.2, 157.5, 156.7, 150.7, 136.7, 129.6, 126.1, 125.3, 117.5, 101.3, 67.5, 63.7, 62.9, 40.7, 40.1, 38.7, 23.2, 17.8, 14.1.

Example 7

Preparation of 2-[2-[[6,6'-diethyl-2,2'-dioxo-7'-[2-(2-prop-2-enoyloxyethylcarbamoyloxy)ethoxy]-4,4'-spirobi[chromane]-7-yl]oxy]ethoxycarbonylamino]ethyl prop-2-enoate

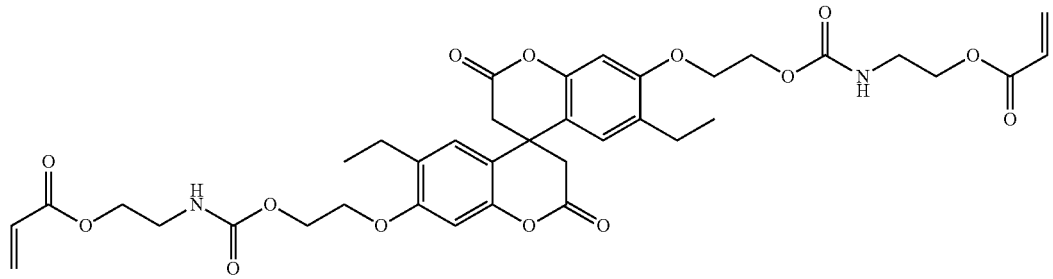 [SMILES: C=CC(=O)OCCNC(=O)OCCOc1cc2c(cc1CC)C1(CC(=O)O2)CC(=O)Oc2cc(OCCOC(=O)NCCOC(=O)C=C)c(CC)cc21]

6,6'-Diethyl-7,7'-bis(2-hydroxyethoxy)-4,4'-spirobi[chromane]-2,2'-dione prepared above (1.044 g, 2.29 mmol) was stirred in THF (10 mL), filtered and then IEA (0.50 mL, 3.9 mmol) was added. The solution was heated to 60° C. and DBTDL (11 IL) added. After 1.5 hours the reaction was allowed to cool and the solvent removed under vacuum overnight. Product was purified by column chromatography (SiO$_2$, 5-20% acetone/chloroform). $^1$H NMR (500 MHz, acetone-d$_6$) δ 6.83 (s, 2H), 6.80 (s, 2H), 6.61 (br s, 2H), 6.34 (dd, J=17.4, 1.5 Hz, 2H), 6.12 (dd, J=17.4, 10.5 Hz, 2H), 5.86 (dd, J=10.3, 1.5 Hz, 2H), 4.43 (m, 4H), 4.29 (m, 4H), 4.18 (t, J=5.6 Hz, 4H), 3.43 (q, J=5.6 Hz, 4H), 3.27 (d, J=15.4 Hz, 2H), 3.01 (d, J=15.4 Hz, 2H), 2.51 (m, 4H), 1.06 (t, J=7.4 Hz, 6H). $^{13}$C NMR (126 MHz, acetone-d$_6$) δ 166.2, 165.8, 157.5, 156.7, 150.7, 130.8, 129.6, 128.8, 126.1, 117.5, 101.3, 67.5, 63.5, 62.9, 40.7, 40.1, 38.7, 23.2, 14.1.

Example 8

Preparation of 2-[[7'-[2-[2-methyl-2-(prop-2-enoylamino)propanoyl]oxyethoxy]-2,2'-dioxo-4,4'-spirobi[chromane]-7-yl]oxy]ethyl 2-methyl-2-(prop-2-enoylamino)propanoate

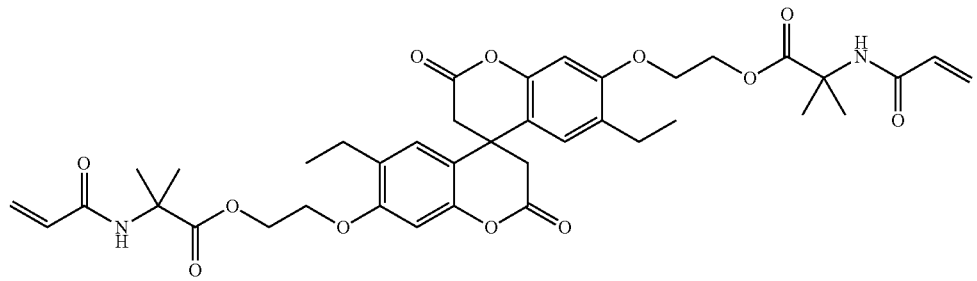 [SMILES: C=CC(=O)NC(C)(C)C(=O)OCCOc1cc2c(cc1CC)C1(CC(=O)O2)CC(=O)Oc2cc(OCCOC(=O)C(C)(C)NC(=O)C=C)c(CC)cc21]

6,6'-Diethyl-7,7'-bis(2-hydroxyethoxy)-4,4'-spirobi[chromane]-2,2'-dione prepared as above (0.509 g, 1.27 mmol) was dissolved in acetone (10 mL) with VDM (0.350 g, 2.57 mmol). 1,8-Diazabicyclo[5.4.0]undec-7-ene (DBU, 10 μL=0.068 mmol) was added and the solution was heated to 60° C. After 48 hours, a further 10 μL DBU was added and heating continued for a further 24 hours. The solution was allowed to cool, then the solvent was removed under vacuum and the product purified by column chromatography (SiO$_2$, 5-20% acetone/CHCl$_3$). 1H NMR (500 MHz, acetone-d$_6$) δ 7.62 (br s, 2H), 6.83 (s, 2H), 6.80 (s, 2H), 6.21 (dd, J=17.2, 10.3 Hz, 2H), 6.07 (dd, J=17.2, 2.1 Hz, 2H), 5.50 (dd, J=10.3, 2.2 Hz, 2H), 4.47 (m, 4H), 4.28 (m, 4H), 3.29 (d, J=15.4 Hz, 2H), 2.99 (d, J=15.4 Hz, 2H), 2.52 (m, 4H), 1.47 (s, 12H) 1.06 (t, J=7.6 Hz, 6H). $^{13}$C NMR (126 MHz, acetone-d$_6$) δ: 174.0, 166.2, 164.4, 157.5, 150.7, 131.5, 129.6, 126.0, 125.4, 117.5, 101.3, 67.0, 63.3, 55.8, 40.7, 38.7, 24.8, 23.2, 14.1.

Example 9

Preparation of 2-[2-[2-[[6,6'-dichloro-7'-[2-[2-[2-(2-methylprop-2-enoyloxy)ethoxy]ethylcarbamoyl-oxy]ethoxy]-2,2'-dioxo-4,4'-spirobi[chromane]-7-yl]oxy]ethoxycarbonylamino]ethoxy]ethyl 2-methyl-prop-2-enoate

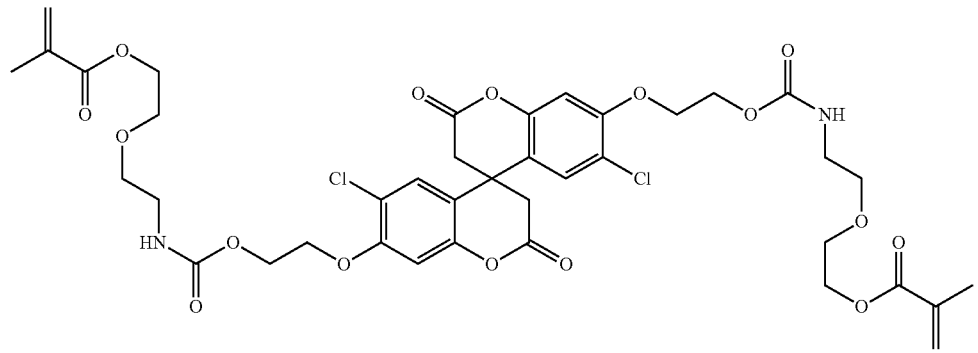 [SMILES: C=C(C)C(=O)OCCOCCNC(=O)OCCOc1cc2c(cc1Cl)C1(CC(=O)O2)CC(=O)Oc2cc(OCCOC(=O)NCCOCCOC(=O)C(=C)C)c(Cl)cc21]

6,6'-Dichloro-7,7'-dihydroxy-4,4'-spirobi[chromane]-2,2'-dione prepared above (0.3065 g, 0.65 mmol) was stirred in ethyl acetate (2 mL). IEEMA (0.231 ml, 1.27 mmol) was added, followed by DBTDL (10 μL, 0.068 mmol) and the reaction mixture heated to 60° C. The solid rapidly dissolved, and after one hour the clear solution was removed from the heat and left to stir at room temperature overnight. The solvent was removed under reduced pressure, and the product purified by column chromatography (SiO$_2$, 5-20% acetone/CHCl$_3$) to give 330 mg of a white foam. $^1$H NMR (500 MHz, acetone-d$_6$) δ 7.10 (s, 2H), 7.05 (s, 2H), 6.35 (br, 2H), 6.06 (s, 2H), 5.61 (p, J=1.5 Hz, 2H), 4.39 (m, 8H), 4.22 (m, 4H), 3.71 (m, 4H), 3.57 (t, J=5.6 Hz, 4H), 3.38 (d, J=15.4 Hz, 2H), 3.28 (m, 4H), 3.14 (d, J=15.4 Hz, 2H), 1.89 (s, 6H). $^{13}$C NMR (126 MHz, acetone-d$_6$) δ 166.9, 165.3, 156.5, 155.6, 151.3, 136.8, 127.1, 125.3, 118.6, 118.5, 103.8, 69.9, 68.8, 68.6, 64.0, 62.6, 40.9, 39.9, 38.7, 17.9.

Example 10

Preparation of 2-[2-[[6,6'-dichloro-7'-[2-[2-(2-methylprop-2-enoyloxy)ethylcarbamoyloxy]ethoxy]-2,2'-dioxo-4,4'-spirobi[chromane]-7-yl]oxy]ethoxycarbonylamino]ethyl 2-methylprop-2-enoate

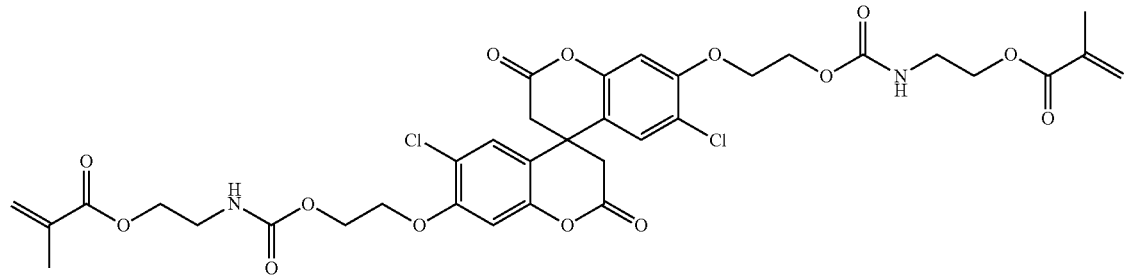 [SMILES: C=C(C)C(=O)OCCNC(=O)OCCOc1cc2c(cc1Cl)C1(CC(=O)O2)CC(=O)Oc2cc(OCCOC(=O)NCCOC(=O)C(=C)C)c(Cl)cc21]

6,6'-Dichloro-7,7'-bis(2-hydroxyethoxy)-4,4'-spirobi[chromane]-2,2'-dione prepared above (0.3 g, 1.07 mmol) was dissolved in ethyl acetate (2 mL). IEMA (0.185 ml, 1.31 mmol) was added, followed by DBTDL (5 μL, 0.008 mmol) and the solution heated to 60° C. for one hour, then left to stir at room temperature overnight. The solvent was removed under reduced pressure, and the product purified by column chromatography (SiO$_2$, 5-20% acetone/CHCl$_3$). $^1$H NMR (500 MHz, acetone-d$_6$) δ 7.08 (s, 2H), 7.05 (s, 2H), 6.64 (br s, 2H), 6.08 (s, 2H), 5.60 (m, 2H), 4.43 (m, 4H), 4.37 (m, 4H), 4.19 (t, J=5.5 Hz, 4H), 3.46 (m, 4H), 3.37 (d, J=15.4 Hz, 2H), 3.14 (d, J=15.4 Hz, 2H), 1.89 (s, 6H). $^{13}$C NMR (126 MHz, acetone-d$_6$) δ 166.9, 165.3, 156.6, 155.6, 151.2, 136.8, 127.1, 125.3, 118.6, 118.5, 103.8, 68.6, 63.8, 62.7, 40.1, 39.9, 38.7, 17.9.

Example 11

Preparation of (2,2'-dioxo-7'-prop-2-enoyloxy-4,4'-spirobi[chromane]-7-yl) prop-2-enoate

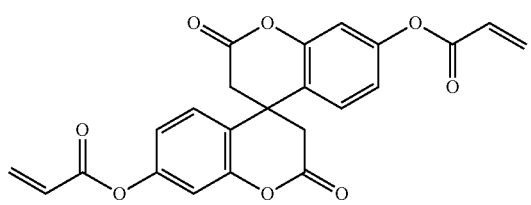 [SMILES: C=CC(=O)Oc1ccc2c(c1)OC(=O)CC21CC(=O)Oc2cc(OC(=O)C=C)ccc21]

7,7'-Dihydroxy-4,4'-spirobi[chromane]-2,2'-dione prepared above (0.496 g, 1.59 mmol) was dissolved in dry dioxane (10 mL) with triethylamine (1.00 mL, 7.2 mmol). Acryloyl chloride (0.50 mL, 6.5 mmol) was added and the reaction mixture stirred overnight, then extracted into 50 mL each of ethyl acetate and deionized water. The organic phase was further extracted with brine, dried with anhydrous MgSO₄, filtered, and the solvent removed under vacuum overnight to yield the desired product as a tan-colored foam (0.56 g). ¹H NMR (500 MHz, acetone-d₆) δ 7.15 (d, J=8.5 Hz, 2H), 7.13 (d, J=2.5 Hz, 2H), 7.08 (dd, J=8.3, 2.2 Hz, 2H), 6.58 (dd, J=17.4, 1.2 Hz, 2H), 6.38 (dd, J=17.4, 10.5 Hz, 2H), 6.14 (dd, J=10.5, 1.2 Hz, 2H), 3.46 (d, J=15.7 Hz, 2H), 3.23 (d, J=15.4 Hz, 2H). ¹³C NMR (126 MHz, acetone-d₆) δ 165.3, 164.0, 152.2, 152.0, 133.3, 127.9, 127.1, 123.3, 118.9, 111.8, 39.8, 39.1.

Example 12

Preparation of (6,6'-diethyl-2,2'-dioxo-7'-prop-2-enoyloxy-4,4'-spirobi[chromane]-7-yl) prop-2-enoate

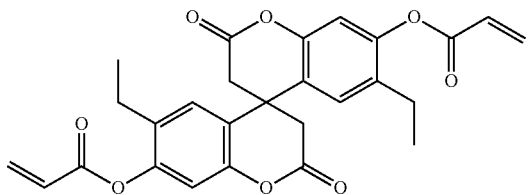 [SMILES: C=CC(=O)Oc1cc2c(cc1CC)C1(CC(=O)O2)CC(=O)Oc2cc(OC(=O)C=C)c(CC)cc21]

6,6'-Diethyl-7,7'-dihydroxy-4,4'-spirobi[chromane]-2,2'-dione prepared above (0.496 g, 1.35 mmol) was dissolved in dry THF (10 mL) with triethylamine (1.20 mL, 8.7 mmol) and cooled in a dry ice/acetone bath. Acryloyl chloride (0.60 mL, 7.8 mmol) was added in five portions over one hour. The reaction mixture was allowed to warm up and stirred overnight, then extracted into 50 mL each of ethyl acetate and deionized water. The organic phase was further extracted with brine, dried with anhydrous Na₂SO₄, filtered, and the solvent removed under vacuum overnight to yield the desired product as a tan-colored foam (0.56 g). ¹H NMR (500 MHz, acetone-d₆) δ 7.07 (s, 4H), 6.62 (dd, J=17.4, 1.2 Hz, 2H), 6.43 (dd, J=17.4, 10.3 Hz, 2H), 6.16 (dd, J=10.3, 1.2 Hz, 2H), 3.44 (d, J=15.4 Hz, 2H), 3.19 (d, J=15.7 Hz, 2H), 2.49 (m, 4H), 1.04 (t, J=7.6 Hz, 6H). ¹³C NMR (126 MHz, acetone-d₆) δ 165.5, 164.1, 150.2, 149.6, 133.3, 130.6, 127.8, 126.9, 123.6, 112.2, 40.0, 39.3, 22.9, 14.1.

Example 13

Preparation of 2-[[6,6'-diethyl-2,2'-dioxo-7'-(2-prop-2-enoyloxyethoxy)-4,4'-spirobi[chromane]-7-yl]oxy]ethylprop-2-enoate

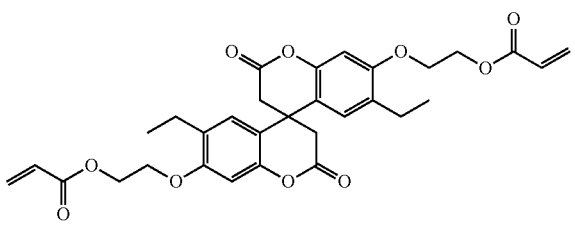 [SMILES: C=CC(=O)OCCOc1cc2c(cc1CC)C1(CC(=O)O2)CC(=O)Oc2cc(OCCOC(=O)C=C)c(CC)cc21]

6,6'-Diethyl-7,7'-bis(2-hydroxyethoxy)-4,4'-spirobi[chromane]-2,2'-dione prepared above (0.679 g, 1.49 mmol) was dissolved in dry THF (5 mL) with triethylamine (1.25 mL, 9.0 mmol) and cooled in a dry ice/acetone bath. Acryloyl chloride (0.35 mL, 4.6 mmol) was added in four portions over 30 minutes. The reaction mixture was allowed to warm up and stirred overnight, then extracted into 50 mL each of ethyl acetate and deionized water. The organic phase was further extracted with brine, dried with anhydrous MgSO₄, filtered, and the solvent removed under vacuum overnight to yield the desired product as a tan-colored foam (0.55 g). ¹H NMR (500 MHz, acetone-d₆) δ 6.84 (m, 4H), 6.39 (dd, J=17.4, 1.2 Hz, 2H), 6.19 (dd, J=17.4, 10.5 Hz, 2H), 5.91 (dd, J=10.3, 1.5 Hz, 2H), 4.56 (m, 4H), 4.38 (m, 4H), 3.25 (d, J=15.7 Hz, 2H), 3.00 (d, J=15.4 Hz, 2H), 2.52 (m, 4H), 1.05 (t, J=7.6 Hz, 6H). ¹³C NMR (126 MHz, acetone-d₆) δ 166.1, 165.7, 157.4, 150.7, 131.0, 129.6, 128.6, 126.2, 117.6, 101.4, 66.9, 62.8, 40.6, 38.7, 23.2, 14.1.

Example 14

Preparation of 7,7'-bis(oxiran-2-ylmethoxy)-4,4'-spirobi[chromane]-2,2'-dione

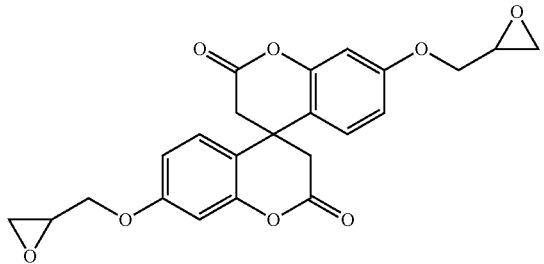 [SMILES: O=C1CC2(CC(=O)Oc3cc(OCC4CO4)ccc32)c2ccc(OCC3CO3)cc2O1]

7,7'-Dihydroxy-4,4'-spirobi[chromane]-2,2'-dione prepared above (1.96 g, 6.28 mmol) was stirred in epichlorohydrin (5.00 mL, 64.8 mmol). Tetrabutylammonium bromide (101 mg, 0.30 mmol) was added and the reaction mixture heated to 110° C. for 40 minutes. The solution was allowed to cool, and then precipitated with diethyl ether (30 mL), the liquid decanted and the solid dried under vacuum. The resulting foam was then dissolved in dichloromethane (20 mL), filtered, and stirred overnight with a 2.5% sodium hydroxide solution (20 mL). The organic phase was separated, extracted with brine, dried over anhydrous sodium sulfate, then filtered and solvent removed under vacuum. The product was purified by column chromatography (SiO₂, 4-20% acetone/CHCl₃) as a mixture of stereoisomers. ¹H NMR (500 MHz, acetone-d₆) δ 6.96 (m, 2H), 6.81 (m, 4H), 4.41 (dt, J=11.2, 2.2 Hz, 2H), 3.92 (m, 2H), 3.30 (m, 4H), 3.06 (d, J=15.4 Hz, 2H), 2.86 (t, J=4.7 Hz, 2H), 2.72 (m, 2H). ¹³C NMR (126 MHz, acetone-d₆) δ 166.6, 159.9, 152.3, 126.7, 118.1, 111.6, 111.5, 103.5, 103.5, 69.8, 69.7, 49.5, 43.5, 39.9, 38.2.

Example 15

Preparation of 6,6'-diethyl-7,7'-bis(oxiran-2-yl-methoxy)-4,4'-spirobi[chromane]-2,2'-dione

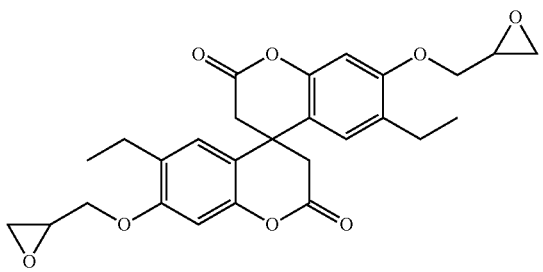 [SMILES: CCc1cc2c(cc1OCC1CO1)OC(=O)CC21CC(=O)Oc2cc(OCC3CO3)c(CC)cc21]

6,6'-Diethyl-7,7'-dihydroxy-4,4'-spirobi[chromane]-2,2'-dione prepared above (2.39 g, 6.49 mmol) was stirred in epichlorohydrin (5.00 mL, 64.8 mmol). Tetrabutylammonium bromide (98.7 mg, 0.30 mmol) was added and the reaction mixture heated to 110° C. for 40 minutes. The solution was allowed to cool and treated with diethyl ether without precipitating. This solution was then precipitated with hexanes (200 mL), the liquid decanted and the solid dried under vacuum. One half of the resulting foam was then dissolved in dichloromethane (20 mL), filtered, and stirred overnight with a 2.5% sodium hydroxide solution (10 mL). The organic phase was separated, extracted with brine, dried over anhydrous sodium sulfate, then filtered and solvent removed under vacuum. 1H NMR (500 MHz, acetone-$d_6$) δ 6.83 (m, 4H), 4.46 (m, 2H), 3.98 (m, 2H), 3.37 (m, 2H), 3.28 (m, 2H), 3.01 (m, 2H), 2.82 (m, 2H), 2.78 (m, 2H), 2.55 (q, J=7.4 Hz, 4H), 1.08 (t, J=7.5 Hz, 6H). $^{13}$C NMR (126 MHz, acetone-$d_6$) δ 166.1, 157.5, 150.7, 129.5, 126.7, 111.7, 117.6, 101.6, 70.0, 69.9, 50.0, 43.8, 40.6, 38.7, 23.2, 14.1.

Example 16

The monomer from Example 3 (50 mg) was dissolved in THF (200 µL) in a 4-mL vial. A solution of AIBN (2 µL, 50 mg/mL in ethyl acetate) was added and the solution degassed with nitrogen. The vial was sealed and heated to 70° C. for 1 hour. A white gel has formed which was insoluble in both THF and acetone.

Example 17

The monomer from Example 7 (52 mg) was dissolved in THF (200 µL) in a 4-mL vial. A solution of AIBN (2 µL, 50 mg/mL in ethyl acetate) was added and the solution degassed with nitrogen. The vial was sealed and heated to 70° C. for 1 hour. A clear gel has formed which was insoluble in both THF and acetone.

Example 18

The monomer from Example 10 (50 mg) was dissolved in THF (200 µL) in a 4-mL vial. A solution of AIBN (2 µL, 50 mg/mL in ethyl acetate) was added and the solution degassed with nitrogen. The vial was sealed and heated to 70° C. for 1 hour. A clear gel has formed which was insoluble in both THF and acetone.

Example 19

The monomer from Example 3 (53 mg) was dissolved in a mixture of THF (200 µL), and 2-ethylhexyl acrylate (200 µL) in a 4-mL vial. A solution of AIBN (2 µL, 50 mg/mL in ethyl acetate) was added and the solution degassed with nitrogen. The vial was sealed and heated to 70° C. for 1 hour. A clear gel has formed which was insoluble in both THF and acetone.

Comparative Example A

2-Ethylhexyl acrylate (200 µL) was dissolved in THF (200 µL) in a 4-mL vial. A solution of AIBN (2 µL, 50 mg/mL in ethyl acetate) was added and the solution degassed with nitrogen. The vial was sealed and heated to 70° C. for 1 hour. No gel was formed.

Example 20

The monomer from Example 7 (48 mg) was dissolved in a mixture of THF (250 µL), and isobornyl acrylate (150 µL) in a 4-mL vial. A solution of AIBN (2 µL, 50 mg/mL in ethyl acetate) was added and the solution degassed with nitrogen. The vial was sealed and heated to 70° C. for 1.5 hours. A clear gel formed which was insoluble in both THF and acetone.

Example 21

The monomer from Example 7 (25 mg) was dissolved in a mixture of THF (250 µL), and isobornyl acrylate (250 µL) in a 4-mL vial. A solution of AIBN (2 µL, 50 mg/mL in ethyl acetate) was added and the solution degassed with nitrogen. The vial was sealed and heated to 70 for 1.5 hours. No gel formed.

Comparative Example B

Isobornyl acrylate (200 µL) was dissolved in THF (200 µL) in a 4-mL vial. A solution of AIBN (2 µL, 50 mg/mL in ethyl acetate) was added and the solution degassed with nitrogen. The vial was sealed and heated to 70° C. for 1 hour. No gel was formed.

Example 22

The monomer from Example 4 (50 mg) was dissolved in THF (200 µL) in a 4-mL vial. A solution of AIBN (2 µL, 50 mg/mL in ethyl acetate) was added and the solution degassed with nitrogen. The vial was sealed and heated to 70° C. for 2 hours, then allowed to cool. A clear gel formed which was insoluble in both THF and acetone.

Example 23

The monomer from Example 8 (50 mg) was dissolved in THF (200 µL) in a 4-mL vial. A solution of AIBN (2 µL, 50 mg/mL in ethyl acetate) was added and the solution degassed with nitrogen. The vial was sealed and heated to 70° C. for 2 hours, then allowed to cool. A clear gel formed which was insoluble in both THF and acetone.

Example 24

The monomer from Example 9 (50 mg) was dissolved in THF (200 µL) in a 4-mL vial. A solution of AIBN (2 µL, 50 mg/mL in ethyl acetate) was added and the solution degassed with nitrogen. The vial was sealed and heated to 70° C. for 2 hours, then allowed to cool. A clear gel formed which was insoluble in both THF and acetone.

Example 25

The monomer from Example 15 (50 mg) was mixed with diethylenetriamine (10 μL) in a 4-mL vial and heated to 70° C. for 2 hours, then allowed to cool. The solid product was insoluble in both THF and acetone.

Example 26 m-Xylylenediamine (18 μL) was added to a solution of the monomer from Example 15 (67 mg) in THF (200 μL) in a 4-mL vial and heated to 70° C. for 30 minutes. A white, rubbery solid formed that was insoluble in both THF and acetone.

Example 27 m-Xylylenediamine (24 μL) was added to a solution of the monomer from Example 14 (80 mg) in THF (200 μL) in a 4-mL vial and heated to 70° C. for 10 minutes. A white precipitate formed that was insoluble in both THF and acetone.

Example 28

Diethylenetriamine (20 μL) was added to a solution of the monomer from Example 14 (80 mg) in THF (200 μL) in a 4-mL vial. A white precipitate formed immediately that was insoluble in both THF and acetone.

Example 29

A dental resin composition was prepared by stirring the components shown in Table 1 at approximately 45° C. until all components were dissolved. A paste was then prepared by combining a 4.00 g quantity of the resin was combined with the components shown in Table 2 in a 40 g DAC cup followed by mixing in a FlakTek DAC Speedmixer for 30 second intervals at 2500 rpm until a uniform homogenous composition was obtained. Shrinkage stress, depth of cure and diametral tensile strength were measured according to the methods described above and the results are reported in Tables 3, 4 and 5, respectively.

TABLE 1

| COMPONENT | Example 29 | Comparative Example C |
|---|---|---|
| | Weight, g | |
| Monomer from Example 1 | 7.00 | 0.00 |
| ERGP-IEM | 0.00 | 6.99 |
| UDMA | 1.92 | 1.91 |
| DDDMA | 0.89 | 0.88 |
| A/F monomer | 0.16 | 0.15 |
| EDMAB | 0.11 | 0.11 |
| CPQ | 0.03 | 0.03 |
| BZT | 0.05 | 0.05 |
| BHT | 0.01 | 0.01 |
| DPIHFP | 0.03 | 0.03 |

TABLE 2

| COMPONENT | WEIGHT, g |
|---|---|
| Resin | 4.00 |
| yoga s/t LE clusters | 7.72 |
| Crystal s/t nanozirconia filler | 0.19 |
| 20 nm Supreme s/t silica filler | 0.35 |
| Sukgyung 100 nm YbF$_3$ | 0.67 |
| Total | 12.93 |

Comparative Example C

A dental resin composition and corresponding paste were prepared by the same procedure as reported in Example 29 was used except that ERGP-IEM was used in place of the monomer from Example 1. Shrinkage stress, depth of cure and diametral tensile strength were measured according to the methods described above and the results are reported in Tables 3, 4 and 5, respectively.

TABLE 3

| | POLYMERIZATION SHRINKAGE STRESS | |
|---|---|---|
| EXAMPLE | Stress (μm) | Standard Deviation |
| Example 29 | 4.10 | 0.31 |
| Comparative Example C | 5.96 | 0.88 |

TABLE 4

| | DEPTH OF CURE | |
|---|---|---|
| EXAMPLE | Stress, μm | Standard Deviation |
| Example 29 | 4.949 | 0.009 |
| Comparative Example C | 5.046 | 0.027 |

TABLE 5

| | DIAMETRAL TENSILE STRENGTH | |
|---|---|---|
| EXAMPLE | Stress, μm | Standard Deviation |
| Example 29 | 70.80 | 4.05 |
| Comparative Example C | 69.44 | 1.68 |

The dental formulation prepared in Example 29, using the monomer from Example 1, displays much reduced shrinkage than Comparative Example C, with similar depth of cure and diametral tensile strength.

All cited references, patents, and patent applications in this application are incorporated by reference in a consistent manner. In the event of inconsistencies or contradictions between portions of the incorporated references and this application, the information in this application shall control. The preceding description, given in order to enable one of ordinary skill in the art to practice the claimed disclosure, is not to be construed as limiting the scope of the disclosure, which is defined by the claims and all equivalents thereto.

What is claimed is:

1. A polymerizable compound represented by the formula

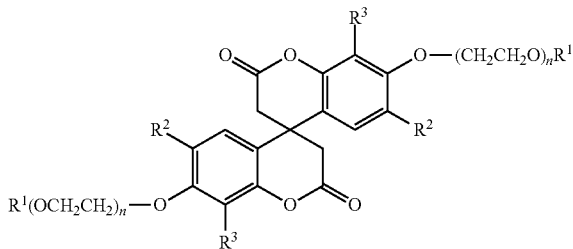

wherein
each $R^1$ independently represents a monovalent group having from 3 to 12 carbon atoms that comprises at least one of an epoxy group, an acryl group, or a methacryl group;
each $R^2$ independently represents H, F, Cl, Br, $C_1$-$C_{12}$ alkyl, $C_2$-$C_3$ carbonylalkyl, or $C_2$-$C_5$ carboalkoxy;
each $R^3$ independently represents H, F, Cl, Br, $C_1$-$C_{12}$ alkyl, $C_2$-$C_3$ carbonylalkyl, or $C_2$-$C_5$ carboalkoxy; and
each n is independently 0, 1, 2, 3, or 4.

2. The polymerizable compound of claim 1, wherein at least one of $R^2$ and $R^3$ is chlorine or bromine.

3. The polymerizable compound of claim 1, wherein each n is 0 or 1.

4. The polymerizable compound of claim 1, wherein at least one $R^1$ is represented by

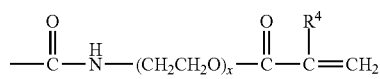

wherein $R^4$ is H or methyl, wherein x is 1 or 2.

5. The polymerizable compound of claim 1, wherein at least one $R^1$ is represented by

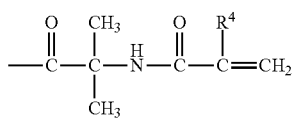

wherein $R^4$ is H or methyl.

6. The polymerizable compound of claim 1, wherein at least one $R^1$ is represented by

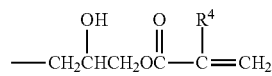

wherein $R^4$ is H or methyl.

7. The polymerizable compound of claim 1, wherein at least one $R^1$ is represented by

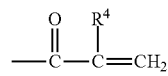

wherein $R^4$ is H or methyl.

8. The polymerizable compound of claim 1, wherein both $R^3$ are H.

9. The polymerizable compound of claim 1, wherein at least one $R^3$ is OH.

10. The polymerizable compound of claim 1, wherein at least one $R^3$ is $C_1$-$C_6$ alkyl.

11. A curable composition comprising:
a polymerizable compound according to claim 1; and
a free radical initiator.

12. The curable composition of claim 11, wherein the free radical initiator comprises a free radical photoinitiator.

13. The curable composition of claim 11, further comprising free radically polymerizable monomer.

14. The curable composition of claim 11, further comprising filler.

15. The polymerizable compound of claim 1, wherein at least one $R^1$ comprises an epoxy group.

16. The polymerizable compound of claim 1, wherein at least one $R^1$ comprises a glycidyl group.

17. A curable composition comprising:
a polymerizable compound according to claim 15; and
a curative for the polymerizable compound.

18. The curable composition of claim 17, further comprising additional epoxy monomer.

19. The curable composition of claim 17, further comprising filler.

20. The curable composition of claim 11, wherein the curable composition is a curable dental restorative composition.

* * * * *